United States Patent
Chapman

(10) Patent No.: US 11,187,710 B2
(45) Date of Patent: Nov. 30, 2021

(54) TIME INDEPENDENT VISCOELASTIC ANALYSIS PARAMETER FOR PREDICTION OF PATIENT OUTCOME

(71) Applicant: The Regents of the University of Colorado, a body corporate, Denver, CO (US)

(72) Inventor: Michael P. Chapman, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 258 days.

(21) Appl. No.: 15/580,968

(22) PCT Filed: Jun. 7, 2016

(86) PCT No.: PCT/US2016/036143
§ 371 (c)(1),
(2) Date: Dec. 8, 2017

(87) PCT Pub. No.: WO2016/200765
PCT Pub. Date: Dec. 15, 2016

(65) Prior Publication Data
US 2019/0072570 A1 Mar. 7, 2019

Related U.S. Application Data

(60) Provisional application No. 62/172,951, filed on Jun. 9, 2015, provisional application No. 62/172,535, filed on Jun. 8, 2015.

(51) Int. Cl.
*G01N 33/86* (2006.01)
*A61B 5/02* (2006.01)
*G01N 11/02* (2006.01)
*G01N 33/49* (2006.01)
*A61B 5/00* (2006.01)
*G01N 11/00* (2006.01)
*G16H 50/70* (2018.01)
*A61B 5/15* (2006.01)
*A61B 5/154* (2006.01)

(52) U.S. Cl.
CPC ............ *G01N 33/86* (2013.01); *A61B 5/00* (2013.01); *A61B 5/02* (2013.01); *G01N 11/00* (2013.01); *G01N 11/02* (2013.01); *G01N 33/4905* (2013.01); *A61B 5/15003* (2013.01); *A61B 5/154* (2013.01); *G16H 50/70* (2018.01)

(58) Field of Classification Search
CPC .... G01N 33/86; G01N 11/00; G01N 33/4905; G01N 11/02; G16H 50/70; A61B 5/00; A61B 5/02; A61B 5/154; A61B 5/15003
USPC .......................................................... 435/13
See application file for complete search history.

(56) References Cited

U.S. PATENT DOCUMENTS

| | | | |
|---|---|---|---|
| 4,529,614 A | 7/1985 | Burns | |
| 4,687,765 A | 8/1987 | Vairel et al. | |
| 4,705,756 A * | 11/1987 | Spillert | G01N 33/50 |
| | | | 435/13 |
| 4,898,825 A | 2/1990 | Morii et al. | |
| 6,472,161 B1 | 10/2002 | Baugh | |
| 7,261,861 B2 | 8/2007 | Kautzky | |
| 7,811,792 B2 | 10/2010 | Cohen et al. | |
| 8,637,320 B2 | 1/2014 | Schubert et al. | |
| 8,772,039 B2 | 7/2014 | Nadkarni | |
| 10,509,512 B2 | 12/2019 | Kikuchi | |
| 2007/0184508 A1 | 8/2007 | Cohen et al. | |
| 2008/0268483 A1 | 10/2008 | Goldenberg et al. | |
| 2009/0130645 A1 | 5/2009 | Schubert et al. | |
| 2010/0062981 A1 | 3/2010 | Jeppsson et al. | |
| 2011/0268732 A1 | 11/2011 | Johansson | |
| 2011/0288732 A1 | 11/2011 | Kuwahara et al. | |
| 2012/0301967 A1 | 11/2012 | Nadkarni | |

(Continued)

FOREIGN PATENT DOCUMENTS

| | | |
|---|---|---|
| EP | 2741086 A1 | 6/2014 |
| JP | 2011518542 A | 6/2011 |

(Continued)

OTHER PUBLICATIONS

Cotton, B. et al. "Rapid Thrombelastography Delivers Real-Time Results That Predict Transfusion Within 1 Hour of Admission" The Journal of Trauma: Injury, Infection, and Critical Care, 71, 2 , Aug. 2011, pp. 407-441. (Year: 2011).*
Sørensen, B. et al. "Whole blood coagulation thrombelastographic profiles employing minimal tissue factor activation" Journal of Thrombosis and Haemostasis, 1, 3, Mar. 2003, pp. 551-558. (Year: 2003).*
Meesters, M, et al. "Instability of the non-activated rotational thromboelastometry assay (NATEM) in citrate stored blood" Thrombosis Reasearch, 136, 2, online May 27, 2015, pp. 481-483. (Year: 2015).*
Sørensen, B. and Ingerslev, J. "Whole blood clot formation phenotypes in hemophilia A and rare coagulation disorders. Patterns of response to recombinant factor VIIa" Journal of Thrombosis and Haemostasis, 2, 2004, pp. 102-110. (Year: 2004).*

(Continued)

*Primary Examiner* — Heidi Reese
(74) *Attorney, Agent, or Firm* — Wilson Sonsini Goodrich & Rosati

(57) ABSTRACT

In some embodiments, the invention provides an in vitro method for identifying a patient as likely as likely to require a transfusion of at least six units of blood in six hours or less. The method comprise, consists essentially of, or consists of (a) analyzing a sample of blood from a patient with a viscoelastic analysis assay to obtain a coagulation characteristic value that is independent of time of the patient; and (b) comparing the coagulation characteristic value of the patient to a coagulation characteristic value that is independent of time of a control,
wherein the coagulation characteristic value of the patient that is lower than the coagulation characteristic value of the control identifies the patient as likely to require a transfusion of at least six units of blood in six hours or less.

17 Claims, 23 Drawing Sheets

(56) References Cited

U.S. PATENT DOCUMENTS

| | | |
|---|---|---|
| 2013/0261171 A1 | 10/2013 | Hessels et al. |
| 2013/0261177 A1 | 10/2013 | Johansson et al. |
| 2015/0316565 A1 | 11/2015 | Chapman et al. |
| 2017/0336423 A1 | 11/2017 | Chapman et al. |
| 2018/0011116 A1 | 1/2018 | Chapman |

FOREIGN PATENT DOCUMENTS

| | | |
|---|---|---|
| JP | 2013543491 A | 12/2013 |
| RU | 2517116 C2 | 5/2014 |
| WO | WO-9614581 A1 | 5/1996 |
| WO | WO-2006036744 A2 | 4/2006 |
| WO | WO-2007047961 A2 | 4/2007 |
| WO | WO-2007047961 A3 | 7/2007 |
| WO | WO-2011057143 A1 | 5/2011 |
| WO | WO-201 2159021 A2 | 11/2012 |
| WO | WO-2014031253 A1 | 2/2014 |
| WO | WO-201 4100378 A1 | 6/2014 |
| WO | WO-201 5171116 A1 | 11/2015 |
| WO | WO-201 6073668 A1 | 5/2016 |
| WO | WO-201 6126849 A1 | 8/2016 |
| WO | WO-201 6200765 A1 | 12/2016 |

OTHER PUBLICATIONS

Gonzalez, E. et al. "Differentiation of Enzymatic from Platelet Hypercoagulability Using the Novel Thrombelastography Parameter Delta (Δ)" Journal of Surgical Research, 103, 1, Sep. 2010, pp. 96-101. (Year: 2010).*

Brohi et al. Acute Coagulopathy of Trauma: Hypoperfusion Induces Systemic Anticoagulation and Hyperfibrinolysis. The Journal of Trauma and Acute Care Surgery, vol. 64, Issue 5, pp. 1211-1217, May 2008.

Brohi et al. Acute Coagulopathy of Trauma: Mechanism, Identification and Effect. Current Opinion in Critical Care, vol. 13, Issue 6, pp. 680-685, Dec. 2007.

Brohi et al. Acute Traumatic Coagulopathy: Initiated by Hypoperfusion, Modulated Through the Protein C Pathway? Annals of Surgery, vol. 245, Nos. pp. 812-818, May 2007.

Chapman et al. Fibrinolysis greater than 3% is the critical value for initiation of antifibrinolytic therapy. J Trauma Acute Care Surg., 75(6), pp. 961-967, Dec. 2013.

Cohen et al. Critical Role of Activated Protein C in Early Coagulopathy and Later Organ Failure, Infection and Death in Trauma Patients. Annals of Surgery, 255 (2) pp. 379-385, Feb. 2012.

Cohen et al. Towards Hemostatic Resuscitation: The Changing Understanding of Acute Traumatic Biology, Massive Bleeding, and Damage-Control Resuscitation. Surg. Clin. NorthAm., vol. 92, Issue 4. Pages 877- 91, Aug. 2012.

Cotton et al. Hyperfibrinolysis at Admission is an Uncommon but Highly Lethal Event Associated with Shock and PreHospital Fluid Administration. Journal of Trauma and Acute Care Surgery, vol. 73, Issue 2, pp. 365-370, Aug. 2012.

Dekker, Simone Esther et al., Lysis Onset Time as Diagnostic Rotational Thromboelastometry Parameter for Fast Detection of Hyperfibrinolysis, Anesthesiology, vol. 121, No. 1, Jul. 2014, pp. 89-97, XP002778643.

Dunn et al. Acidosis-Induced Coagulopathy. Surg. Forum, 30, pp. 471-473, Jan. 1979.

Eastridge et al. Died of Wounds on the Battlefield: Causation and Implications for Improving Combat Casualty Care. Journal of Trauma, 71 (1 Suppl.): S4-8, Jul. 2011.

EP16747211.7 Extended European Search Report dated Jun. 1, 2018.

Extended European Search Report dated Jan. 24, 2020 for EP Patent Appl. No. 17803282.7.

Extended European Search Report relating to EP Appl. No. 15856414.6 dated Mar. 14, 2018.

Ganter, et al., Coagulation monitoring: current techniques and clinical use of viscoelastic point-of-care coagulation devices. Anesthesia & Analgesia, May 2008;106(5): 1366-1375.

Geier, Bruno et al., Pharmacokinetics of tissue plasminogen activator in an isolated extracorporeal circuit, J. Vascular Surgery, 2001, vol. 33, No. 1, pp. 165-169.

Gonzalez et al. Fresh Frozen Plasma Should be Given Earlier to Patients Requiring Massive Transfusion. Journal of Trauma Injury, Infection, and Critical Care. 62(1), pp. 112-119, 2007.

Hirsh et al. Management of deep vein thrombosis and pulmonary embolism. A statement for healthcare professionals. Council on Thrombosis (in consultation with the Council on Cardiovascular Radiology), American Heart Association. Circulation. Jun. 15, 1996;93(12):2212-45.

Holcomb, et al., Admission rapid thrombelastography can replace conventional coagulation tests in the emergency department. Ann Surg, 2012;256: 476-486.

International Preliminary Report on Patentability dated Nov. 22, 2018 for PCT/US2017/32226.

International Search Report and Written Opinion dated Jan. 14, 2016 for International PCT Patent Application No. PCT/US2015/059146.

International Search Report and Written Opinion dated Jun. 30, 2016 for International PCT Patent Application No. PCT/US2016/016412.

International Search Report and Written Opinion dated Aug. 23, 2017 for International PCT Patent Application No. PCT/US2017/032226.

International Search Report and Written Opinion dated Aug. 26, 2016 for International PCT Patent Application No. PCT/US2016/036143.

Johansson, et al., Current management of massive hemorrhage in trauma. Scandinavian Journal of Trauma, resuscitation and emergency medicine, 2012;20(47): 1-10.

Johnson et al. Effect of Blood Products Transfusion on the development of Post Injury Multiple Organ Failure. Achieves of Surgery, 145(10), pp. 973-977, 2010.

Kashuk et al. Major Abdominal Vascular Trauma-A Unified Approach, Journal of Trauma, 22(8), pp. 672-679, Aug. 1982.

Kashuk et al. Post Injury Life Threatening Coagulopathy: Is 1:1 Fresh Frozen Plasma: Packed Red Blood Cells The Answer? Journal of Trauma, Infection, and Critical Care, 65(2), pp. 261-271,2008.

Moore et al. Blood Transfusion: An Independent Risk Factor for Post Injury Multiple Organ Failure. Archives of Surgery, 132(6), pp. 620-624, Jun. 1997.

Moore et al. Hyperfibrinolysis, physiologic fibrinolysis, and fibrinolysis shutdown: The spectrum of postinjury fibrinolysis and relevance to antifibrinolytic therapy. J Trauma Acute Care Surg., 77(6), pp. 811-817, Dec. 2014.

Neal et al. Massive Transfusion: An Evidence-Based Review of Recent Developments. Archives of Surgery, 147(6), pp. 563-571,2012.

Non-Final Office Action dated Oct. 25, 2019 for U.S. Appl. No. 15/524,095.

Pham, et al., Update on massive transfusion. British journal of anaesthesia. 2013;111(S1): i71-782.

Semon et al. Thromboelastography (TEG) in Trauma. Department of Surgical Education, Orlando Medical Center, 7 pages, Dec. 3, 2014.

Watson et al. Fresh Frozen Plasma is Independently Associated with a Higher Risk of Multiple Organ Failure and Acute Respiratory Distress Syndrome. Journal of Trauma, 67(2), pp. 221-227, I Aug. 2009.

Whiting, David et al., TEG and ROTEM: Technology and clinical applications, American Journal of Hematology, vol. 89, No. 2, Feb. 2014, pp. 228-232, XP002778641.

* cited by examiner

Novel parameters dAmax and Acrit

TIME INDEPENDENT VISCOELASTIC ANALYSIS PARAMETER FOR PREDICTION OF PATIENT OUTCOME

CROSS-REFERENCE TO RELATED APPLICATIONS

This application is a National Stage Entry of PCT/US2016/036143, filed Jun. 7, 2016 which claims priority to U.S. provisional patent application No. 62/172,535 filed Jun. 8, 2015 and to U.S. provisional patent application No. 62/172,951 filed Jun. 9, 2015, the entire contents of which are hereby incorporated by reference.

BACKGROUND OF THE INVENTION

The present invention relates to the fields of medicine and surgery, and emergent and chronic critical care for traumatic injury.

Following a traumatic injury (e.g., gunshot wound, car accident, or during surgery), uncontrolled hemorrhage (i.e., uncontrolled bleeding) is a leading cause of early death (Eastridge et al., J. of Trauma. 71(1 Suppl): S4-8, 2011; Gonzalez et al., J. of Trauma. 62(1):112-9, 2007; Kashuk et al., J. of Trauma 65(2):261-71, 2008). Trauma induced coagulopathy (TIC) is an exacerbating phenomenon observed in many cases of massive hemorrhage, and current practice emphasizes hemostatic resuscitation with blood components (Brohi et al., Current Opinion in Critical Care 13(6): 680-685, 2007; Brohi et al., Annals of Surgery 245(5): 812-818, 2007; Brohi et al., J. of Trauma, 64(5): 1211-1217, 2008; Cohen et al., Annals of Surgery 255(2): 379-385, 2012; Cotton et al., J. of Trauma and Acute Care Surgery 73(2):365-70, 2012; Dunn et al., Surg. Forum. 30:471-3, 1979). This practice is geared at not only replacing lost oxygen carrying capacity, but in reestablishing normal coagulation and forestalling the "bloody vicious cycle" of hemorrhagic shock, acidosis/hypothermia and coagulopathy (Kashuk et al., J. of Trauma 22(8):672-9, 1982; Cohen et al., Surg. Clin North Am. 92(4):877-91, 2012). Establishment, by hospital blood banks, of massive transfusion protocols (MTPs) to aid in efficient hemostatic resuscitation of patients with life-threatening hemorrhage, represents an important development in trauma systems management and has been shown to reduce mortality in massively bleeding patients.

Triggering a massive transfusion protocol (MTP) activation, however, is not without potentially negative consequences. Transfusion of blood or blood products consume large amounts of scarce medical resources (e.g. universal donor blood components either transfused or wasted) as well as exposing patients to the risks of transfusion of multiple units of blood products, empirically and potentially needlessly unless patients who truly require an MTP activation are chosen accurately (Johnson et al., Archives of Surgery 145(10):973-7, 2010; Moore et al., Archives of Surgery 132(6):620-4, 1997; Watson et al., J. of Trauma. 2009 August; 67(2):221-7; discussion 8-30, 2009; Neal et al., Archives of Surgery. 147(6):563-71, 2012).

Thus, there is a need to distinguish patients in massive hemorrhage who truly need a transfusion protocol from those patients who do not.

Viscoelastic analysis methods such as thrombelastography (TEG) and thromboelastometry (TEG) are robust and versatile diagnostic systems for point-of-care diagnosis of coagulopathy. However, application of these analysis methods in high acuity settings such as trauma and emergency surgery has been limited by the time it takes the test to yield a result with regard to clot strength, a key parameter for interpretation of the overall clotting performance of the patient's blood.

It would be useful to have rapid methods and parameters to accurately predict final clot strength and/or identify those patients who need transfusion of blood or blood products.

SUMMARY OF THE EMBODIMENTS

The invention provides new parameters from viscoelastic analyses of blood that are not dependent upon time.

In a first aspect, the invention provides an in vitro method for identifying a patient as likely to require a transfusion of at least six units of blood in six hours or less, the method comprising, consisting essentially of, or consisting of obtaining a coagulation characteristic value that is independent of time by using a viscoelastic analysis assay to analyze a sample of blood from the patient, wherein the coagulation characteristic value of the patient that is lower than a coagulation characteristic value that is independent of time of a control (such as a healthy volunteer) identifies the patient as likely to require a transfusion of at least six units of blood in six hours or less.

In some embodiments, the coagulation characteristic value that is independent of time of a control is obtained by analyzing a sample of blood from the control with a viscoelastic analysis assay. In some embodiments, the control is a healthy volunteer. In some embodiments, the control is a population of patients and the coagulation characteristic value of the control is the mean coagulation characteristic value of the population.

In some embodiments, the sample of blood is not supplemented with a clotting factor or an enhancer of clot formation. In some embodiments, the coagulation characteristic value that is independent of time is Acrit. In some embodiments, the coagulation characteristic value that is independent of time is dAmax.

In some embodiments, the coagulation characteristic value that is independent of time is obtained not more than twenty minutes after the start of the viscoelastic analysis of the sample of blood from the patient. In some embodiments, the coagulation characteristic value is obtained not more than fifteen minutes after the start of the viscoelastic analysis of the sample of blood from the patient. In some embodiments, the coagulation characteristic value that is independent of time is obtained not more than ten minutes after the start of the viscoelastic analysis of the sample of blood from the patient. In some embodiments, the coagulation characteristic value that is independent of time is obtained not more than fifteen minutes after the start of clot formation in the sample of blood from the patient. In some embodiments, the coagulation characteristic value that is independent of time is obtained not more than ten minutes after the start of clot formation in the sample of blood from the patient. In some embodiments, the coagulation characteristic value is obtained not more than five minutes after the start of clot formation in the sample of blood from the patient.

In some embodiments, the patient is human. In some embodiments, the patient is a trauma patient.

In some embodiments, the viscoelastic analysis assay is performed using a thromboelastography analyzer system. In some embodiments, the viscoelastic analysis assay is performed using a thromboelastometry analyzer system.

In some embodiments, the coagulation characteristic value that is independent of time of the patient that is at least 1.5 times lower than the coagulation characteristic value that is independent of time of the control (e.g., a healthy volunteer or a population of patients) identifies the patient as likely to require a transfusion of at least six units of blood in six hours or less. In some embodiments, the coagulation characteristic value of the patient that is at least 1.5 times lower than the coagulation characteristic value of the control (e.g., a healthy volunteer or a population of patients) identifies the patient as likely to require a transfusion of at least ten units of blood in six hours or less.

In some embodiments, the coagulation characteristic value that is independent of time is obtained by fitting a tracing from the viscoelastic analysis assay of the same sample of blood from the patient to a tracing from the model $dA/dT=aA^2/(e^{bA}-1)$. In some embodiments, the coagulation characteristic value that is independent of time is obtained by taking an area under a tracing from the viscoelastic analysis assay of the same sample of blood from the patient from a start of clot formation to a maximum amplitude.

In another aspect, the invention provides an in vitro method for identifying a patient as likely as likely to require a transfusion of at least six units of blood in six hours or less, the method comprising, consisting essentially of, or consisting of (a) analyzing a sample of blood from a patient with a viscoelastic analysis assay to obtain a coagulation characteristic value that is independent of time of the patient; and (b) comparing the coagulation characteristic value of the patient to the coagulation characteristic value of the control, wherein the coagulation characteristic value of the patient that is lower than the coagulation characteristic value of the control (e.g., a healthy volunteer) identifies the patient as likely to require a transfusion of at least six units of blood in six hours or less.

In some embodiments, the coagulation characteristic value that is independent of time of a control is obtained by analyzing a sample of blood from the control with a viscoelastic analysis assay. In some embodiments, the control is a healthy volunteer. In some embodiments, the control is a population of patients and the coagulation characteristic value of the control is the mean coagulation characteristic value of the population.

In some embodiments, the sample of blood is not supplemented with a clotting factor or an enhancer of clot formation. In some embodiments, the coagulation characteristic value that is independent of time is Acrit. In some embodiments, the coagulation characteristic value that is independent of time is dAmax.

In some embodiments, the coagulation characteristic value that is independent of time is obtained not more than twenty minutes after the start of the viscoelastic analysis of the sample of blood from the patient. In some embodiments, the coagulation characteristic value that is independent of time is obtained not more than fifteen minutes after the start of the viscoelastic analysis of the sample of blood from the patient. In some embodiments, the coagulation characteristic value is obtained not more than ten minutes after the start of the viscoelastic analysis of the sample of blood from the patient. In some embodiments, the coagulation characteristic value that is independent of time is obtained not more than five minutes after the start of the viscoelastic analysis of the sample of blood from the patient.

In some embodiments, the coagulation characteristic value that is independent of time is obtained not more than fifteen minutes after the start of clot formation in the sample of blood from the patient. In some embodiments, the coagulation characteristic value that is independent of time is obtained not more than ten minutes after the start of clot formation in the sample of blood from the patient. In some embodiments, the coagulation characteristic value that is independent of time is obtained not more than five minutes after the start of clot formation in the sample of blood from the patient.

In some embodiments, the patient is human. In some embodiments, the patient is a trauma patient.

In some embodiments, the viscoelastic analysis assay is performed using a thromboelastography analyzer system. In some embodiments, the viscoelastic analysis assay is performed using a thromboelastometry analyzer system.

In some embodiments, the coagulation characteristic value that is independent of time of the patient that is at least 1.5 times lower than the coagulation characteristic value that is independent of time of the control (e.g., a healthy volunteer or a population of patients) identifies the patient as likely to require a transfusion of at least six units of blood in six hours or less. In some embodiments, the coagulation characteristic value of the patient that is at least 1.5 times lower than the coagulation characteristic value of the control (e.g., a healthy volunteer or a population of patients) identifies the patient as likely to require a transfusion of at least ten units of blood in six hours or less.

In some embodiments, the coagulation characteristic value that is independent of time is obtained by fitting a tracing from the viscoelastic analysis assay of the same sample of blood from the patient to a tracing from the model $dA/dT=aA^2/(e^{bA}-1)$. In some embodiments, the coagulation characteristic value that is independent of time is obtained by taking an area under a tracing from the viscoelastic analysis assay of the same sample of blood from the patient from a start of clot formation to a maximum amplitude.

In yet another aspect, the invention provides an in vitro method for determining an amount of fibrinogen in a patient comprising: (a) obtaining a coagulation characteristic value that is independent of time of a sample of blood from the patient using a viscoelastic analysis assay and (b) plotting the patient coagulation characteristic value against a standard table of coagulation characteristic values of blood samples of healthy volunteers with known amounts of fibrinogen to determine the amount of fibrinogen in the sample of blood from the patient.

In some embodiments, the coagulation characteristic value that is independent of time is dAmax. In some embodiments, the patient is human.

In still another aspect, the invention provides an in vitro method for determining a quantity of platelets in a patient comprising: (a) obtaining a coagulation characteristic value that is independent of time of a sample of blood from the patient using a viscoelastic analysis assay and (b) plotting the patient coagulation characteristic value against a standard table of coagulation characteristic values of blood samples of healthy volunteers with known quantities of platelets to determine the quantity of platelets in the sample of blood from the patient.

In some embodiments, the coagulation characteristic value is a product of dAmax and Acrit. In some embodiments, the patient is human.

BRIEF DESCRIPTION OF THE DRAWINGS

The foregoing features of embodiments will be more readily understood by reference to the following detailed description, taken with reference to the accompanying drawings, in which:

FIG. 5A is a TEM tracing in the presence of the EXTEM reagent, which allows assessment of clot formation, fibrin polymerization, and fibrinolysis via the extrinsic pathway. FIG. 5B is a TEM tracing the presence of the FIBTEM reagent, which blocks platelets. Thus, FIG. 5B shows an assessment of the clot firmness of a fibrin clot. As FIGS. 5A and 5B show, platelet and fibrinogen contribution to clot strength are not additive.

FIG. 6A shows the classic TEG tracing. Note that this tracing in FIG. 6A is the upper half of the full TEG tracing, with amplitude (in mm) on the Y axis and time (in minutes) on the X axis. The point at which the amplitude is increasing most rapidly is depicted as the Acrit parameter. In FIG. 6A, the Acrit occurs when A (the amplitude) is 11.64. The derivative of this new parameter Acrit, namely dA, is 0.68. FIG. 6B is a curve showing the dA (derivative of amplitude) on the Y axis plotted against amplitude (in mm) on the Y axis. FIG. 6C shows the position of Acrit on the tracings of FIG. 6A and FIG. 6B. Thus, FIG. 6C shows that the Acrit parameter is when dA is 0.68 mm and A is 11.74 mm.

FIG. 6A is a TEG tracing from a healthy human volunteer (namely, patient no. 20074B). FIG. 6A shows the Acrit (with a dA at 0.66 and an A (amplitude) at 13.65 mm) which occurs at approximately 17.0 minutes. Additionally.

DETAILED DESCRIPTION OF SPECIFIC EMBODIMENTS

Figure 1:
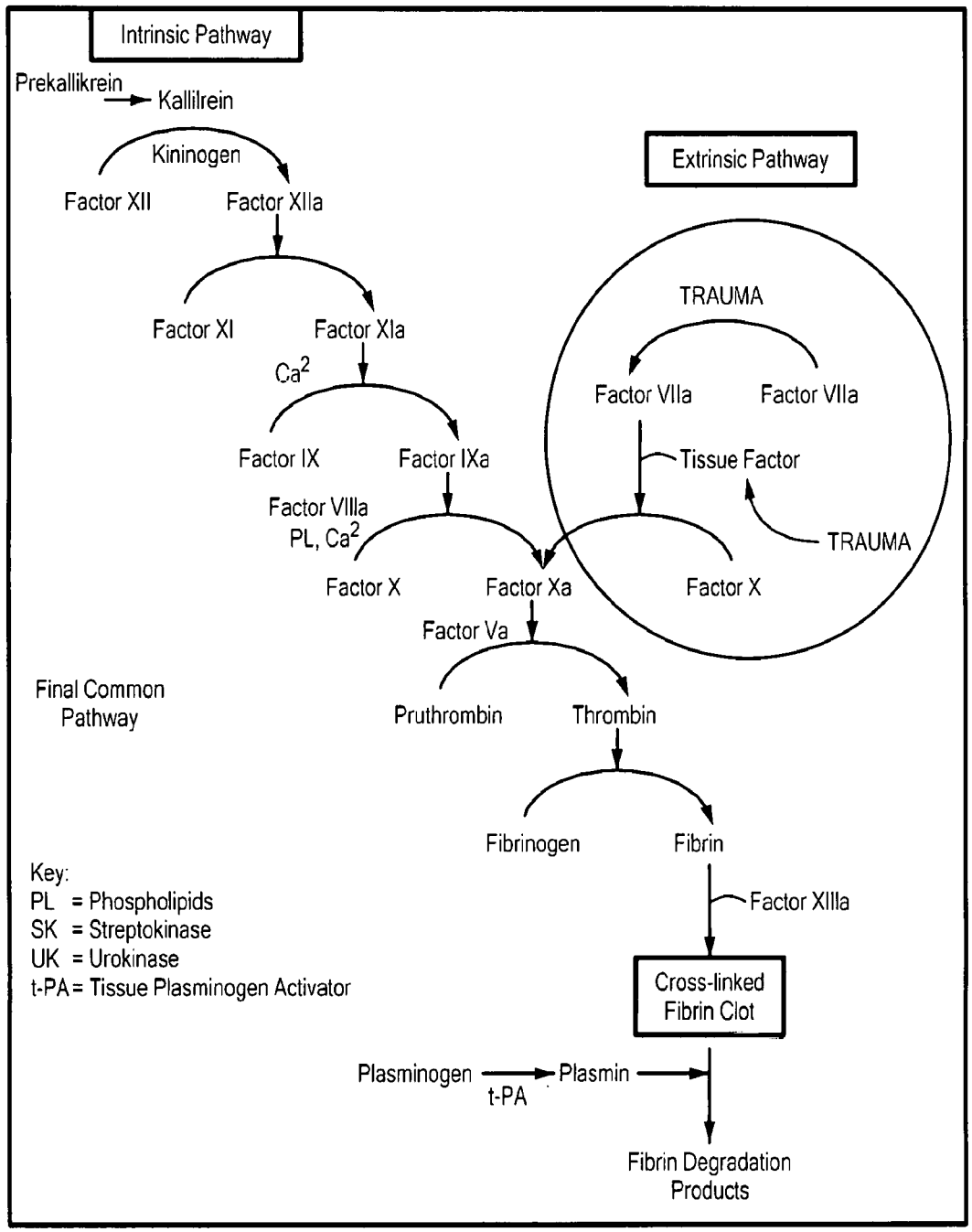
FIG. 1 is a schematic diagram showing the clotting cascade that leads eventually to the formation of a blood clot. The contributions of the intrinsic and extrinsic pathway to the blood clot are shown.

The invention stems, in part, from the discovery of very rapid in vitro methods to reliably and accurately identify patients who are likely need a blood transfusion. The publications (including patent publications), web sites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

The further aspects, advantages, and embodiments of the invention are described in more detail below. The definitions used in this specification and the accompanying claims shall following terms shall have the meanings indicated, unless the context clearly otherwise requires. Any conflict between an art-understood definition of a word or phrase and a definition of the word or phrase as specifically taught in this specification shall be resolved in favor of the latter. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Haemostasis is a tightly regulated process which causes bleeding to stop. In the body, circulating blood remains fluid under normal conditions, but forms localized clots when the integrity of the vascular system is breeched. Trauma, infection, and inflammation all activate the blood's clotting system, which depends on the interaction of two separate systems: enzymatic proteins in a clotting cascade (e.g., clotting factors such as Factor VII or Factor IX) and activated platelets. The two systems work in concert to plug defects in the broken vessels.

A blood clot (also called a thrombus) that forms during haemostasis is made of two parts—a platelet plug and a mesh of cross-linked fibrin protein. The fibrin results from cleavage of fibrinogen into fibrin by thrombin which is activated during the clotting cascade (see FIG. 1). A blood clot needs to be of sufficient strength to resist dislodgement by circulating blood or mechanical movement. If a particular clotting factor is dysfunctional or absent, as in hemophilia, an insufficient amount of fibrin forms. Similarly, massive consumption of clotting factors in a trauma situation decreases the amount of fibrin formed and can lead to uncontrolled hemorrhage. Inadequate numbers of platelets resulting from trauma, surgery, or chemotherapy also decrease platelet aggregation, as do genetic disorders, uremia, or salicylate therapy. Ultimately, reduced fibrin formation or platelet aggregation results in clots of inadequate tensile strength. This hypocoagulable state makes the patient prone to bleeding. Conversely, endothelial injury, stasis, cancer, genetic diseases, or other hypercoagulable states lead to thrombosis (i.e., blood clot) formation, exemplified in deep-vein thromboses, pulmonary emboli, and arterial occlusions such as stroke and myocardial infarction.

When a trauma patient is brought into a treatment center such as an emergency room, uncontrolled hemorrhage can lead to death. However, a recent analysis of data from a three year study of resuscitation strategies of patients (whose inclusion criteria included activation of an MTP) revealed that only 46% of patients, for whom an MTP was activated based upon the judgment of the attending trauma surgeon, actually went on to require a massive transfusion (defined as >10 units or packed red blood cells [PRBCs] in 6 hours). It is clear that clinician judgment leaves much to be desired in terms of accuracy of prediction of massive transfusion requirement. Additionally, recent experience with the design of several prospective trials related to trauma resuscitation have highlighted the difficulty in early, prospective selection of patients truly at high risk of major hemorrhage and coagulopathy (Brasel et al., Journal of the American College of Surgeons. 2008 February; 206(2):220-32, 2008; Bulger et al., Archives of surgery. 2008 February; 143(2):139-48; discussion 49); Bulger et al., Annals of surgery. 2011 March; 253(3):431-41; and Raab et al., Critical care medicine. 2008 November; 36(11 Suppl):S474-80).

Given the scarcity of donor blood (and blood products) and the potential risks associated from receiving a donor blood product (e.g., recipient immune response to the donor blood or recipient exposure to pathogens or contaminants in the donor blood), attempts have been made to develop new parameters, or repurpose existing parameters, in order to rapidly and accurately predict which patients are in need of a blood transfusion (e.g., with blood or a blood product). Such patients can be identified, for example, by determining clot strength of a blood sample taken from the patient.

Thus, in some embodiments, the invention provides in vitro methods for identifying a patient likely to suffer a massive hemorrhage (i.e., those patients who will require a transfusion of at least 10 units of blood in 6 hours or less, or who will bleed to death). In some embodiments, the method comprises obtaining a coagulation characteristic value that is independent of time using a viscoelastic analysis assay to analyze a sample of blood taken from the patient, wherein the coagulation characteristic value of the patient that is lower than a specified threshold (e.g., to some degree lower than that of a healthy volunteer or lower than the mean coagulation characteristic value of a population of patients) predicts that the patient is likely to suffer a massive hemorrhage. Early prediction of massive hemorrhage can be lifesaving as it allows the clinician to initiate massive transfusion protocol or other resuscitative interventions in a timely manner.

In some embodiments, the methodology described herein can be used to rapidly discriminate the origin of the coagulopathy leading to the massive hemorrhage as being with a defect in platelet or fibrinogen function.

The invention stems, in part, from the identification of a coagulation characteristic value derived from data obtained from analyzing patient blood samples using viscoelastic analyses. Such viscoelastic analyses include, without limitation, thromboelastography (TEG) and thromboelastometry (TEM).

As used herein, by "blood sample" or "sample of blood" is meant a sample of blood taken, for example, from a patient. The patient may be a human, but may also be any other animal (e.g., veterinary animal or exotic animal). Blood is the circulating tissue of an organism that carries oxygen and nutritive materials to the tissues and removes carbon dioxide and various metabolic products for excretion. Blood (often called whole blood) consists of a pale yellow or gray yellow fluid, plasma, in which are suspended red blood cells, white blood cells, and platelets. Some practitioners consider blood to be an organ. However, all agree that how quickly blood will clot is discernible from a sample of blood. It is a matter of analyzing the sample correctly to determine how the blood (e.g., cells and proteins in the blood) will clot. While current technology is limited by how quickly such information can be deduced from a sample of blood, in some embodiments, the present invention allows for such information to be obtained very quickly.

In some embodiments, as the term is used herein, by "blood" is meant whole blood, or a portion of whole blood, or a blood product (e.g., packed red blood cells). The blood in the blood sample taken from a patient (e.g., a trauma patient or a healthy volunteer) may thus be a sample of whole blood or a sample of a portion of blood or a sample of a blood product. The blood (e.g., blood in a blood sample) may be untreated, or may be treated. For example, a blood sample may be citrated blood (e.g., whole blood collected into a 3.5 mL container containing 3.2% citrate). The blood (e.g., blood in a blood sample) may also be a sample of platelet rich plasma. The blood (e.g., blood in a blood sample) may also be heparinized blood or may be a blood sample treated with protamine to reverse the effects of heparin. In some embodiments, the blood sample is not supplemented with a clotting factor (e.g., thrombin) and/or is not supplemented with an enhancer of clot formation (e.g., kaolin). The blood (e.g., blood in a blood sample) may be fresh, frozen, or stored according to standard methods (e.g., stored at 4° C. in a blood storage solution such as the storage solution described in U.S. Pat. No. 8,709,707). Thus, when blood refers to one or more components of whole blood, any of these components may be treated. Thus, blood (e.g., blood in a blood sample) may be platelets, packed red blood cells, heparinized packed red blood cells, citrated blood, plasma or platelet-free plasma taken from the blood of the patient. In some embodiments, the blood (e.g., blood in a blood sample) may be a sample that has reduced platelet function. For example, the blood (e.g., blood in a blood sample) may be treated with an inhibitor of platelet function such as cytochalasin D.

Note that by "blood transfusion" or simply "transfusion" is meant administration (e.g., by intravenous route) of blood (as defined above) to a recipient patient. The blood transfused to the patient can be fresh, or frozen, and can be whole blood, citrated blood, packed red blood cells, platelets, and so forth. Typically, blood is administered in units, where one unit of blood is roughly equal to one pint of whole blood. Note that the unit of blood may be a unit of packed red blood cells, but that unit of packed red blood cells is still equivalent to approximately one pint of whole blood for the donor. In some embodiments, the transfusion given to the patient is matched to the patient's ABO profile (e.g., O type blood donated to A patient, B patient, or AB patient, or B type blood donated to B or AB patient).

By "viscoelastic analysis" or "viscoelastic analysis assay" is meant any in vitro analysis method that measures the characteristics of elastic solid (e.g., fibrin solids) and fluids. In other words, viscoelastic analysis allows the study of properties of a viscous fluid, such as blood or a blood sample taken from a patient (e.g., a human patient). By using viscoelastic analysis, the mechanical strength of an evolving blood clot can be measured in vitro.

In some embodiments, the viscoelastic analysis is performed under conditions that mimic the conditions in vivo that govern hemostasis. Hemostasis is a tightly regulated, extremely complex process involving many interacting factors, which include coagulation and fibrinolytic proteins, activators, inhibitors and cellular elements, such as platelet cytoskeleton, platelet cytoplasmic granules and platelet cell surfaces, that controls bleeding in the body of an individual (e.g., a human individual). Hemostasis includes and comprises the balance between two processes: (1) the coagulation process, namely blood coagulation by formation of a fibrin-containing blood clot, and (2) the fibrinolysis process, namely the process involved in the breakdown of that clot, for example, by activation of plasmin to dissolve the fibrin mesh holding the clot together.

For example, the condition may include a temperature that mimics a body temperature (e.g., a temperature of 37° C.). The condition may also include clot formation and dissolution at flow rates that mimic those found in blood vessels.

Various devices that perform thromboelastography, and methods for using these devices, are described in U.S. Pat. Nos. 5,223,227; 6,225,126; 6,537,819; 7,182,913; 6,613,573; 6,787,363; 7,179,652; 7,732,213; 8,008,086; 7,754,489; 7,939,329; 8,076,144; 6,797,419; 6,890,299; 7,524,670; 7,811,792; 20070092405; 20070059840; 8,421,458; US 20120301967; and U.S. Pat. No. 7,261,861, the entire disclosures of each of which are hereby expressly incorporated herein by reference.

Thromboelastography (TE) monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the kinetics, strength and stability of the clot provides information about the ability of the clot to perform "mechanical work," i.e., resisting the deforming shear stress of the circulating blood. In essence, the clot is the elementary machine of hemostasis. Hemostasis instruments that measure hemostasis are able to measure the ability of the clot to perform mechanical work throughout its structural development. These hemostasis analyzers measure continuously all phases of patient hemostasis as a net product of whole blood components in a non-isolated, or static fashion from the time of test initiation until initial fibrin formation, through clot rate strengthening and ultimately clot strength through clot lysis.

In some embodiments, the viscoelastic analysis and/or the hemostasis analyzer comprises a container which is in contact with the blood.

As used herein, by "container" is meant a rigid surface (e.g., a solid surface), a portion of which contacts a portion of a blood sample placed into the container at any point during the viscoelastic analysis. The portion of the container that contact the portion of blood sample may also be referred to as the "interior" of the container. Note that the phase "into the container" does not mean that the container has a bottom surface which is in contact with the portion of the blood sample. Rather, the container can be a ring-shaped structure, where the inside of the ring is the interior of the container, meaning that the inside of the ring is the portion of the ring-shaped container that contacts a portion of the blood sample. A blood sample can flow into the container and be held there, for example, by vacuum pressure or surface tension.

Still additional types of containers that are included in this definition are those present on plates and cassettes (e.g., a microfluidic cassette), where the plate or cassette has multiple channels, reservoirs, tunnels, and rings therein. Each of the contiguous channels (comprising, for example, a channel, a reservoir, and a ring) is a container, as the term is used herein. Hence, there may be multiple containers on one cassette. U.S. Pat. No. 7,261,861 (incorporated herein by reference) describes such a cassette with multiple channels or containers. Any of the surfaces in any of the channels or tunnels of the cassette may be an interior of the container if that surface comes into contact with any portion of the blood sample, at any time during the viscoelastic analysis.

Additional non-limiting hemostasis analyzer instruments are described in U.S. Pat. No. 7,261,861; US Patent Publication No. US20070092405; and US Patent Publication No. US20070059840.

A non-limiting analyzer instrument that performs viscoelastic analysis using thromboelastography is the TEG thromboelastograph hemostasis analyzer system sold commercially by Haemonetics, Corp. (Braintree, Mass.).

Figure 2A:
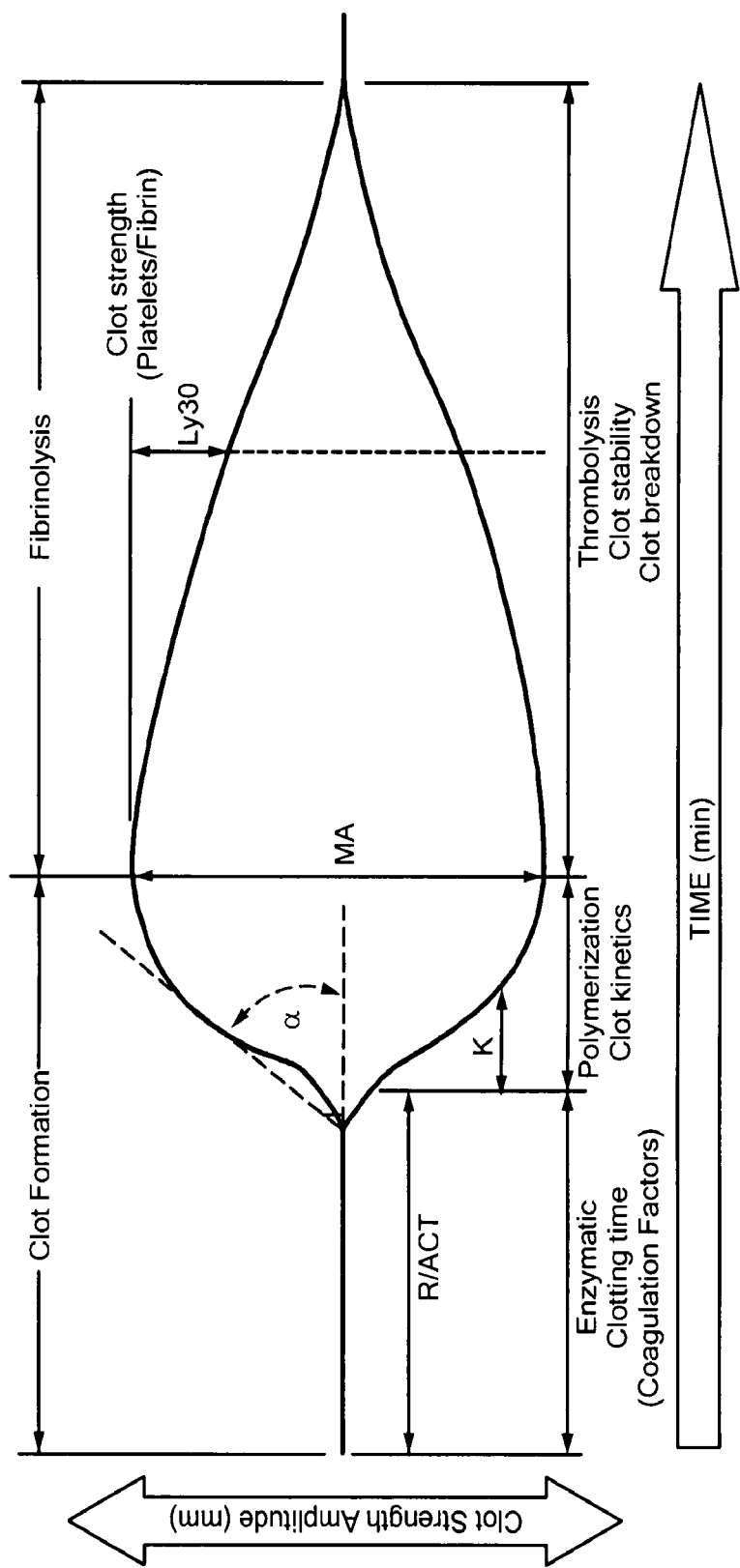
FIG. 2A is a schematic diagram showing a thromboelastography (TEG) tracing or curve. As the upper and lower portions of the tracing are mirror images of each other, TEG tracings are sometimes depicted as just the upper half of the tracing. The time from assay initiation is the dependent variable (on the x-axis) and the amplitude of coupling of the motion of the reaction cup to a centrally suspended pin (a proxy for viscoelastic clot strength) is the readout variable, on the y-axis, in units of millimeters. The events leading up to maximum amplitude (MA) of the clot are the clot formation stage, and following the MA is the clot dissolution stage or fibrinolysis stage.

Thus, the TEG assay may be performed using the TEG thromboelastograph hemostasis analyzer system that measures the mechanical strength of an evolving blood cloth. To run the assay, the blood sample is placed into a container (e.g., a cup or a cuvette), and a metal pin goes into the center of the container. Contact with the interior walls of the container (or addition of a clot activator to the container) initiates clot formation. The TEG thromboelastograph hemostasis analyzer then rotates the container in an oscillating fashion, approximately 4.45 degrees to 4.75 degrees, every 10 seconds, to imitate sluggish venous flow and activate coagulation. As fibrin and platelet aggregates form, they connect the inside of the container with the metal pin, transferring the energy used to move the container in the pin. A torsion wire connected to the pin measures the strength of the clot over time, with the magnitude of the output directly proportional to the strength of the clot. As the strength of the clot increases over time, a classic TEG tracing curve develops (See FIG. 2A, where clot strength is reflected on the Y axis and time is on the X axis).

Where there is a pin in the TEG analyzer, the rotational movement of the pin is converted by a transducer to an electrical signal, which can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile. Such a configuration of the computer is well within the skills of one having ordinary skill in the art. As shown in FIG. 2A, the resulting hemostasis profile (i.e., a TEG tracing curve) is a measure of the time it takes for the first fibrin strand to be formed, the kinetics of clot formation, the strength of the clot (measured in millimeters (mm) and converted to shear elasticity units of dyn/cm 2) and dissolution of clot. See also Donahue et al., *J. Veterinary Emergency and Critical Care:* 15(1): 9-16. (March 2005), herein incorporated by reference The descriptions for several of these measured parameters shown in FIG. 2A are well known and have been described elsewhere (see, e.g., Kouerinis et al., *Interactive Cardiovascular and Thoracic Surgery* 7: 560-563, 2008; Walsh et al., J. of Extracorporeal Tech. 43(3): 162-167, 2011; and Galvez and Cortes, Revista Colombiana Anestesiol. 40: 224-230, 2012; all incorporated by reference herein in their entireties).

Briefly, ACT (or R) is the time is the period of time of latency from the time that the blood sample is placed in the TEG analyzer until the initial clot formation. This is typically takes about 4-8 minutes in a healthy person. For patients in a hypocoagulable state (i.e., a state of decreased coagulability of blood), the ACT (or R) number is longer (i.e., higher), while in a hypercoagulable state (i.e., a state of increased coagulability of blood), the ACT (or R) number is shorter.

K value (measured in minutes) is the time from the end of ACT until the clot reaches 20 mm. The K value represents the speed of clot formation. This K value is about 0 to about 4 minutes (i.e., after the end of ACT) in a healthy person. In a hypocoagulable state, the K number is longer, while in a hypercoagulable state, the K number is shorter.

α measures the rapidity of fibrin build-up and cross-linking (clot strengthening). Thus, it shows the rate at which a solid clot is formed. It is angle between the line formed from the split point tangent to the curve and the horizontal axis, and represents the kinetics of clot development. This angle is typically about 47° to 74°. In a hypocoagulable state, the a degree is lower, while in a hypercoagulable state, the α degree is higher.

MA or Maximum Amplitude in mm, is a direct function of the maximum dynamic properties of fibrin and platelet bonding and represents the ultimate or maximum strength of the clot. The MA number (also referred to herein as Amax) is the greatest diameter of the clot and a measure of the clot's elasticity. This number is typically from about 54 mm to about 72 mm in a normal individual, and the MA occurs typically between about 15 to about 35 minutes after the start of the viscoelastic assay. Note that if the blood sample tested has a reduced platelet function, this MA represents the strength of the clot based on fibrin only. Decreases in MA may reflect a hypocoagulable state (e.g., with platelet dysfunction or thrombocytopenia), whereas an increased MA (e.g., coupled with decreased R) may be suggestive of a hypercoagulable state.

Figure 2B:
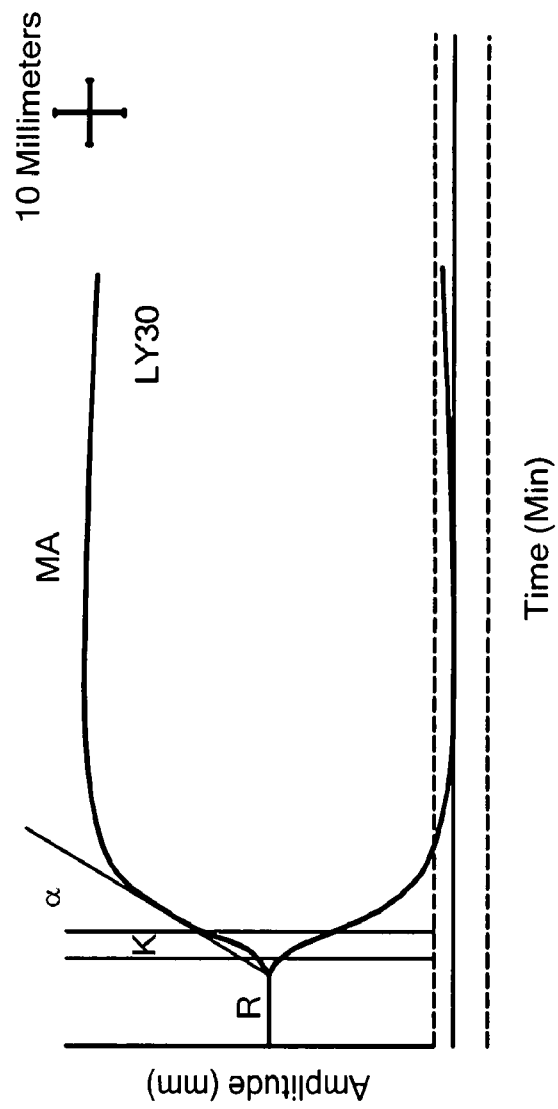
FIG. 2B is a schematic diagram showing a TEG tracing from a healthy human volunteer. Note that in a healthy volunteer, fibrinolysis is very gradual.

LY30 measures the rate of amplitude reduction 30 minutes after MA and represents clot retraction, or lysis. The LY30 is, therefore, the percentage of lysis of the clot or a percentage decrease in amplitude 30 minutes after the MA. The LY30 can also be described as the loss of potential area of under the TEG curve. For example, if the amplitude of the curve did not decrease following the peak at MA, the LY30 would be 0%. In healthy individuals, this LY30 number is typically 0% to about 8% (see FIG. 2B). In some embodiments, a hypocoagulable state is present if the LY30 is greater than 7.5%. In some embodiments, an LY30 that is greater than 6%, or greater than about 5%, or greater than about 4%, or greater than about 3.5%, or greater than about 3% identifies a patient with a hypocoagulable state.

Another viscoelastic hemostasis assay that can be used is the thromboelastometry ("TEM") assay. This TEM assay may be performed using the ROTEM Thromboelastometry Coagulation Analyzer (TEM International GmbH, Munich, Germany), the use of which is well known (See, e.g., Sorensen, B., et al., *J. Thromb. Haemost.* 2003. 1(3): p. 551-8. Ingerslev, J., et al., *Haemophilia* 2003. 9(4): p. 348-52. Fenger-Eriksen, C, et al, *Br J Anaesth,* 2005. 94(3): p. 324-9]. In the ROTEM analyzer, the blood sample is placed into a container (also called a cuvette or cup) and a cylindrical pin is immersed. Between pin and the interior wall of the container there is a gap of 1 mm which is bridged by the blood. The pin is rotated by a spring to the right and the left. As long as the blood is liquid (i.e., unclotted), the movement is unrestricted. However, when the blood starts clotting, the clot increasingly restricts the rotation of the pin with rising clot firmness. The pin is connected to an optical detector. This kinetic is detected mechanically and calculated by an integrated computer to the typical tracing curves (TEMogram) and numerical parameters (see FIG. 3).

Figure 3:
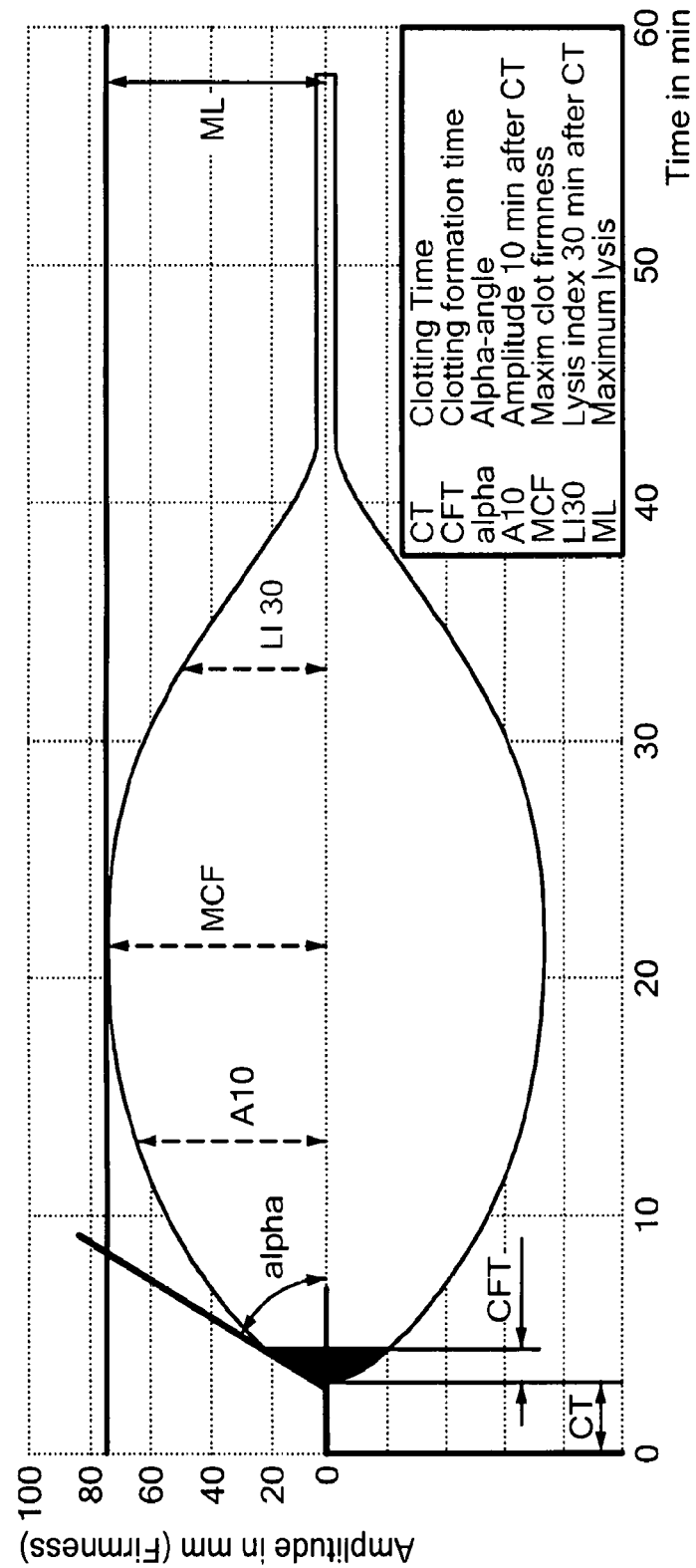
FIG. 3 is a schematic diagram showing a thromboelastometry (TEM) tracing or curve. As the upper and lower portions of the tracing are mirror images of each other, TEM tracings are sometimes depicted as just the upper half of the tracing. The events leading up to maximum clot firmness (MCF) of the clot are the clot formation stage (or coagulation stage), and following the MA is the clot dissolution stage or fibrinolysis stage.

In the ROTEM Thromboelastometry Coagulation Analyzer, the movement of the pin can be monitored by a computer including a processor and a control program. The computer is operable on the electrical signal to create a hemostasis profile corresponding to the measured clotting process. Additionally, the computer may include a visual display or be coupled to a printer to provide a visual representation of the hemostasis profile (called a TEMogram. Such a configuration of the computer is well within the skills of one having ordinary skill in the art. As shown in FIG. 3, the resulting hemostasis profile (i.e., a TEM tracing curve) is a measure of the time it takes for the first fibrin strand to be formed, the kinetics of clot formation, the strength of the clot (measured in millimeters (mm) and converted to shear elasticity units of dyn/cm 2) and dissolution of clot. The descriptions for several of these measured parameters are as follows:

CT (clotting time) is the period of time of latency from the time that the blood was placed in the ROTEM analyzer until the clot begins to form. In some embodiments, the CT time is the period of time from when the blood is placed on the ROTEM analyzer to when the amplitude reaches 1 mm wide.

CFT (Clot formation time): the time from CT until a clot firmness of 20 mm point has been reached. In FIG. 3, this CFT time is depicted as the time immediately following CT. CFT is reflective of the speed of clot formation.

alpha-angle: The alpha angle is the angle measured between the midline of the tracing and a line drawn from the 1 mm point tangential to the curve. This parameter is reflective of the speed of clot formation.

MCF (Maximum clot firmness): MCF is the greatest vertical amplitude of the trace. MCF reflects the absolute strength of the fibrin and platelet clot.

A10 (or A5, A15 or A20 value). This value describes the clot firmness (or amplitude) obtained after 10 (or 5 or 15 or 20) minutes after the clotting time (CT). In other words, and provide a forecast on the expected MCF value at an early stage.

LI 30 (Lysis Index after 30 minutes). The LI30 value is the percentage of remaining clot stability in relation to the MCF value at 30 min after CT.

ML (Maximum Lysis). The ML parameter describes the percentage of lost clot stability (relative to MCF, in %) viewed at any selected time point or when the test has been stopped.

A low LI 30 value or a high ML value indicates hyperfibrinolysis. While in normal blood fibrinolysis activity is quite low, in clinical samples a more rapid loss of clot stability by hyperfibrinolysis may lead to bleeding complications which can be treated by the administration of antifibrinolytic drugs.

Thus, parameters of interest in TEG or TEM assays include the maximum strength of the clot which is a reflection of clot strength. This is the MA value in the TEG assay, and the MCF value in the TEM assay. The reaction time (R) in TEG (measured in sec) and clotting time (CT) in TEG is the time until there is first evidence of clot; clot kinetics (K, measured in minutes) is a parameter in the TEG test indicating the achievement of clot firmness; and a in TEG or alpha-angle in TEM is an angular measurement from a tangent line drawn to the curve of the TEG tracing or TEM tracing starting from the point of clot reaction time that is reflective of the kinetics of clot development. (See Trapani, L. M. Thromboelastography: Current Applications, Future Directions", Open Journal of Anesthesiology 3(1): Article ID: 27628, 5 pages (2013); and Kroll, M. H., "Thromboelastography: *Theory and Practice in Measuring Hemostasis,*" *Clinical Laboratory News: Thromboelastography* 36(12), December 2010; instruction manuals for the TEG instrument (available from Haemonetics, Corp.), and the instruction manual for the ROTEM instrument (available from TEM International GmbH), all of which documents are herein incorporated by reference in their entireties.

In some embodiments, the parameters (and hence the coagulation characteristics) are recorded by observation of different excitation levels of the sample as coagulation occurs. For example, where the container is a microfluidic cassette, or a particular channel in the cassette, the blood sample may be excited at a resonant frequency and its behavior observed by an electromagnetic or light source as coagulation occurs. In other embodiments the sample's coagulation characteristics may be observed for changes with a light source without exciting the sample.

Because a single cassette may have multiple containers (e.g., different channels in the cassette), the sample in a container contacted with an inhibitor of fibrinolysis is easily directly comparable to a sample in a container (e.g., in an adjacent channel in the same microfluidic cassette) that is not contacted with the inhibitor of fibrinolysis.

When no fibrinolysis occurs, the amplitude value at the MA on a TEG tracing and the amplitude value at the MCF on a TEM tracing stays constant or may decrease slightly due to clot retraction. However, as fibrinolysis occurs (e.g., in a hypocoagulable state), the curve of the TEG tracing and the TEM tracing starts to decay. The resultant loss in potential area-under-the-curve in the 30 minutes following Maximum Amplitude in the TEG assay is called the LY30 (see FIG. 2A). LY30, the percentage of lysis 30 minutes after the maximum amplitude point (expressed as a percentage of the clot lysed) and clot firmness (G, measured in dynes/$cm^2$), indicates the rate of clot lysis. The corresponding value in the TEM assay is the LI30 value (see FIG. 3).

The LY30 is the usual metric of fibrinolysis. However, this parameter has some limitations including lack of sensitivity and specificity. Most importantly, the LY30 parameter takes at least 30 minutes to obtain. In normal patients, obtaining the LY30 in at least thirty minutes (because the 30 minutes must be added to whatever the time it took the clot to form in the first place) is adequate. However, in trauma patients, waiting the at least 30 minutes to determine if the patient's blood is clotting normally may be detrimental to the patient's outcome (e.g., the patient may bleed to death).

Figure 4:
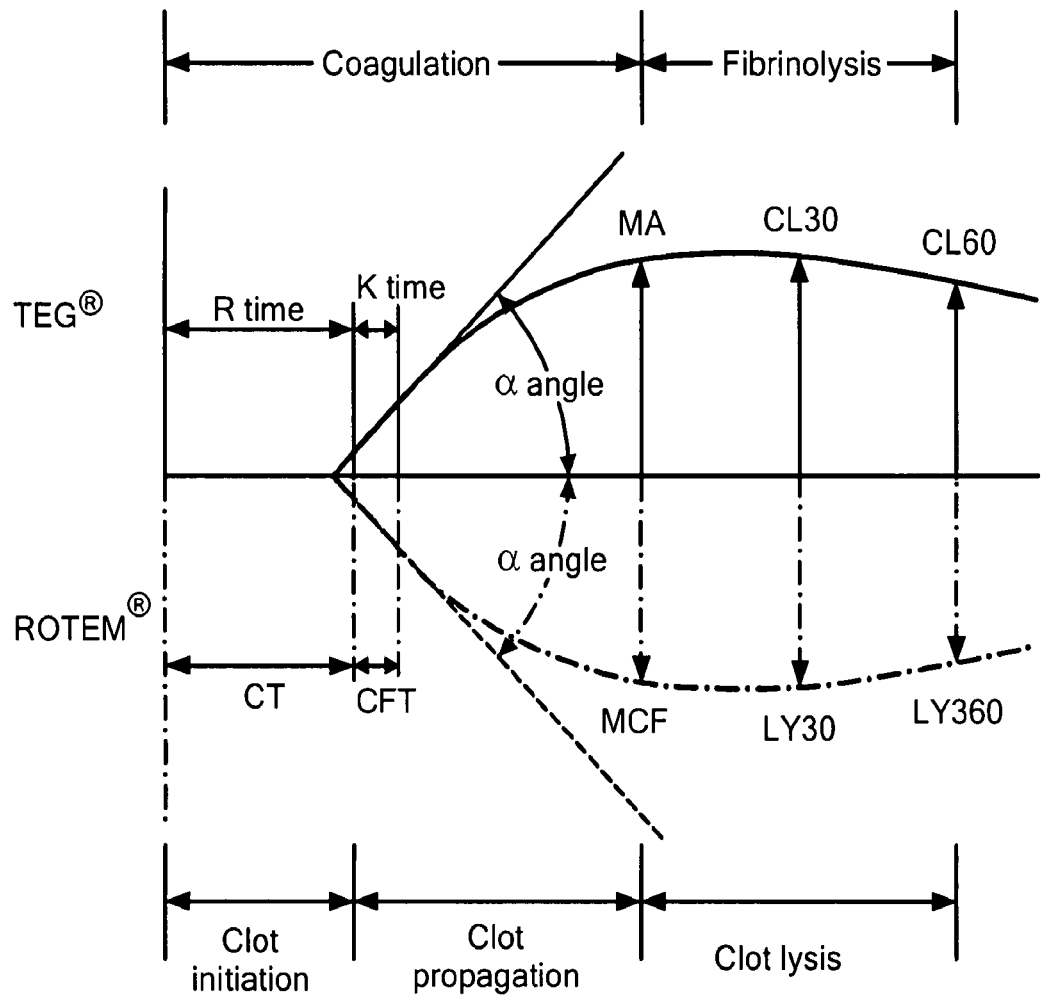
FIG. 4 is a schematic drawing showing a side-by-side comparison of a TEG tracing (top half of figure) and a TEM tracing (bottom half of figure). As is clear from FIG. 4, the R value in a TEG tracing is equivalent to a clotting time (CT) value in a TEM tracing, the K value in a TEG tracing is equivalent to a clot formation time (CFT) value in a TEM tracing, the MA value in a TEG tracing is equivalent to a MCF value in a TEM tracing.

Thus, viscoelastic assays such as TEG and TEM measure the mechanical strength of the evolving blood clot over time. As the strength of the blood clot increases over time, a classic TEG curve (FIG. 2A) or classic TEM curve (see FIG. 3) develops. FIG. 4 provides a convenient side by side comparison of the TEG curves (upper part of the figure from a TEG apparatus) and TEM curves (lower part of the figure from a ROTEM apparatus). Note that for both TEG and TEM, sometimes only the upper half of the curve is depicted (see, for example, the TEG curve depicted in FIG. 7A).

Figure 5B:
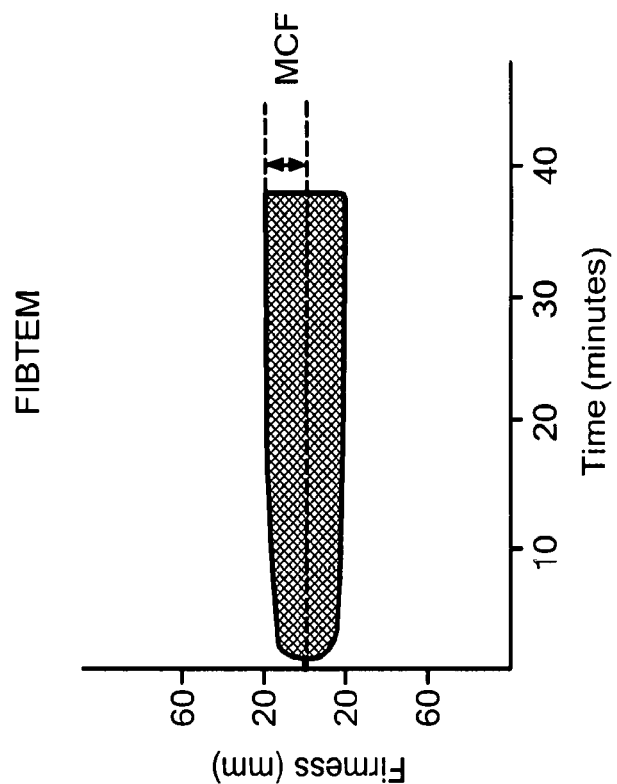
FIGS. 5A and 5B are two TEM tracings.
Figure 5A:
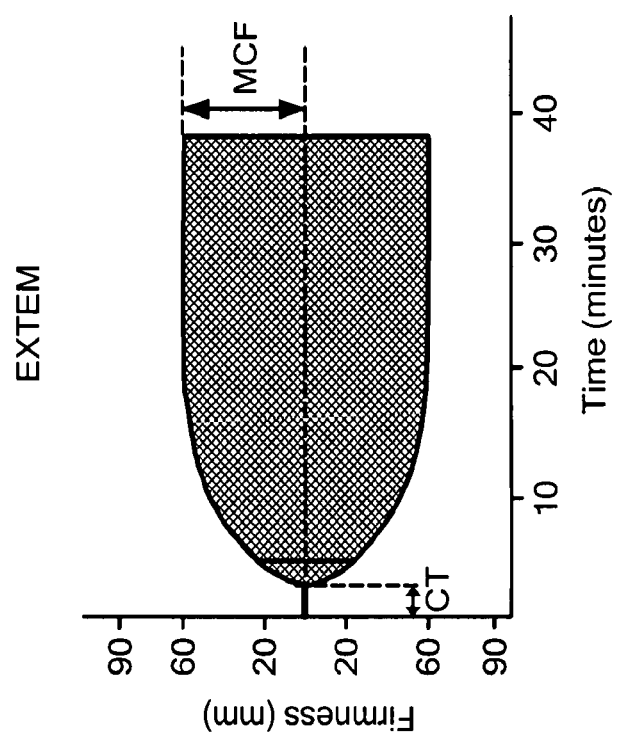

There are, however, drawbacks to using the standard TEG and TEM assays. For example, it is difficult to measure the contributions of platelets and fibrinogen to the clot. Currently, the assays such as EXTEM and platelet-inhibitor containing FIBTEM (see FIGS. 5A and 5B, respectively) are run to try to determine the contributions of platelets and fibrinogen to clot strength. However, simple subtraction of assays run with and without platelet inhibitors is not an accurate measure of the contributions of platelets and fibrinogen because as FIGS. 5A and 5B show, platelet and fibrinogen contribution to clot strength is not additive.

Figure 7A:
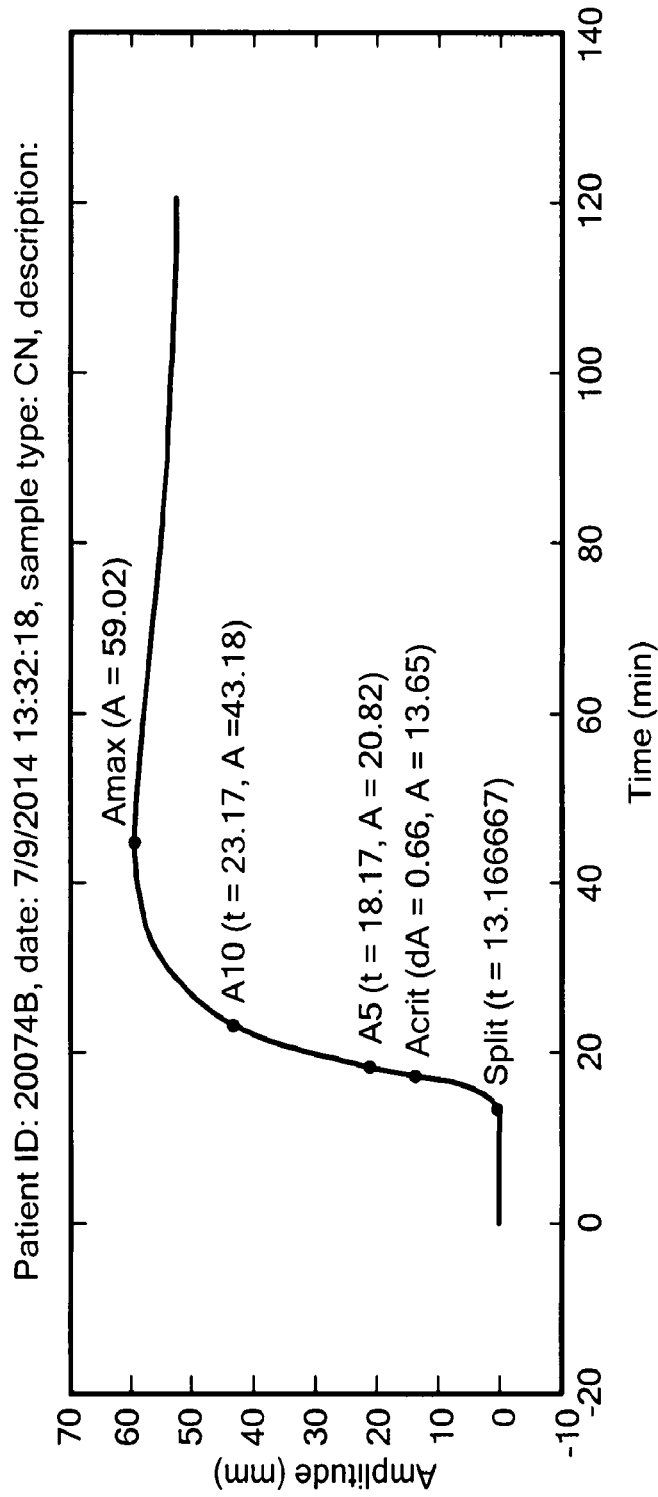
FIG. 7A shows the split time (at t (time)=13.166667 minutes), A5 (at t=18.17 min and A=20.82 mm), A10 (at 5=23.17 min and A=43.18 mm, and Amax (i.e., the MA) at A=59.02 mm). In the patient shown in FIG. 7A, Amax occurs at approximately 42 minutes.

Furthermore, perhaps the biggest drawback of all of the above listed parameters of TEG and TEM is the amount of time needed to obtain them. For example, while the MA (or MCF) and the LY30 (or LI30) in TEG and the MCF in TEM are considered two of the more important measurements of the clot in their respective assays, they are by definition obtainable only after the assay has been running for some time. For example, the LY30 and LI30 parameters are obtainable thirty minutes after the MA or MCF which, themselves, are obtainable after the R/ACT time and K time in the TEG assay, and after the CT time and the CFT time in the TEM assay. In the healthy volunteer whose data is depicted in FIG. 7A, Amax (i.e., MA) is not obtainable until 42 minutes after the start of the TEG analysis. During treatment of an individual with a traumatic injury (e.g., a person who has been in a car accident), minutes can make the difference between a positive outcome and a negative one.

Figure 5C:
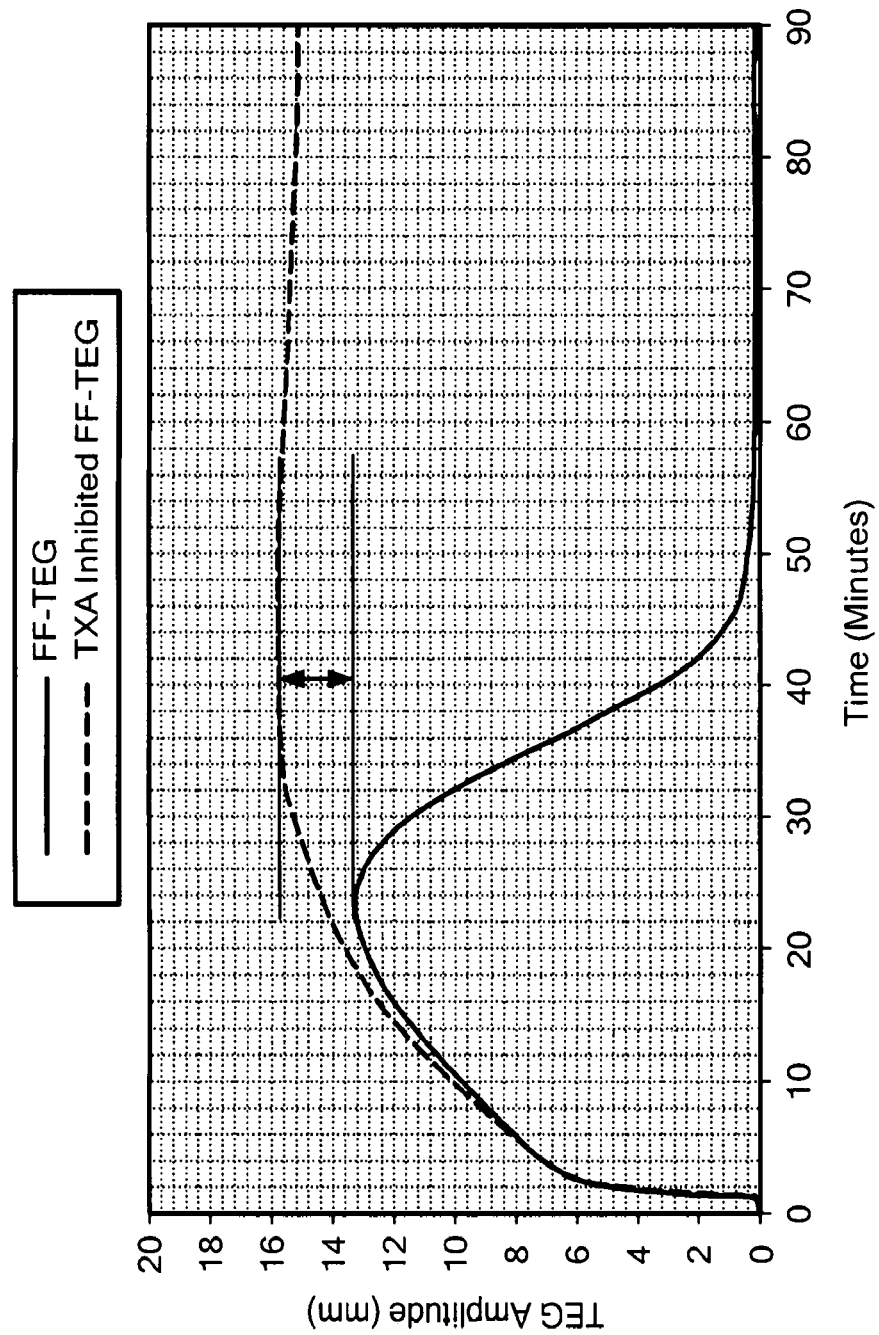
FIG. 5C is a schematic diagram showing a TEG tracing from a functional fibrinogen assay (green line) compared to the TEG tracing from a functional fibrinogen assay for a sample treated with tranexamic acid (TXA), an antifibrinolytic agent that blocks the action of plasminogen (blue line). As can be seen, in the presence of hyperfibrinolysis (as simulated by the addition of TXA) may obscure and lower the MA, as depicted in red parallel bars in FIG. 5C by the difference between the peaks of the green line and the blue line.

Additionally, as FIG. 5C shows, if the patient has hyperfibrinolysis, an accurate reading of MA may be impossible. In this FIG. 5C, the antifibrinolytic agent tranexamic acid (TXA) is added to a blood sample to simulate a hyperfibrinolytic condition. As FIG. 3C shows, the true MA (i.e., Amax) is never reached in the hyperfibrinolysis sample, because the clot starts breaking down too soon. Yet accurate reading of the MA is very important for determining patient outcome.

The invention therefore stems, in part, from the desire to develop parameters that predict MA on a rational physical basis and encompass enough of the early TEG tracing to accurately predict its future trajectory. Results of earlier observational studies indicated that a major source of noisiness in the predictive value of early TEG parameters was the position of the parameters with respect to time as the dependent variable. As the rate of clot formation feeds back into the independent variable, the TEG curve shape is difficult to model over a wide dynamic range. Moreover, the inherent physics of clot formation are in essence time independent but are describable by the instantaneous state of the clot structure and concentration of the catalytic and stoichiometric participants in clot formation.

Thus, in some embodiments, the invention provides a model of clot formation in a time-independent domain, wherein TEG amplitude (A) is a proxy for clot strength and thus instantaneous clot structure and the instantaneous rate of clot formation at that state (dA/dT) becomes the dependent variable, such that:

$$dA/dT = f(A)$$

This function clearly defines the "accelerative" versus "coasting" phases of clot formation, a novel reconstitution of the traditional notions of initiation versus propagation in a non-temporal domain.

The implied function dA/dT=f(A) is then modeled using a physical model that bore a resemblance to the data derived from the human healthy volunteers. That physical model is:

$$dA/dT = aA^2/(e^{bA} - 1)$$

which is a lower order modification of Planck's equation which contains only two fitting coefficients, namely a and b. Note that the values for a and b will vary in each patient. The values for a and b are how the fitting is done.

In some embodiments, A is the value of the Amplitude, e is a mathematical constant that is approximately 2.71828, a is a patient-specific coefficient derived from fitting that patient's data to the empirically derived equation using a least squares method (a well-established data fitting method), and b is also a patient-specific coefficient derived from fitting that patient's data to the empirically derived equation using a least squares method. In some embodiments, coefficient a=0.011 and coefficient b=0.104. In some embodiments, A goes from 0 to 60.

The invention, in some embodiments, therefore provides time-independent parameters. One such parameter is dAmax for the maximum in the rate of change of A. Thus, just as MA is the maximum amplitude is the time-domain TEG curve the global maximum in the time independent TEG curve is dAmax. Note that "Amax" and "MA" are interchangeable terms and both refer to the maximum amplitude. The corresponding amplitude of dAmax called the critical amplitude or Acrit. In taking a derivative of the TEG curve, the derivative of Acrit appears at the peak of a curve plotting dA versus amplitude (in mm). Acrit occurs when dA is at its maximum value (i.e., Acrit occurs at dAmax). See, for example, FIG. 6C.

Accordingly, in a first aspect, the invention provides a method for identifying a patient likely to require a transfusion of at least six units of blood in six hours, the method comprising obtaining a coagulation characteristic value that is independent of time by using a viscoelastic analysis assay to analyze a sample of blood from the patient, the coagulation characteristic value obtained not more than fifteen minutes after the start of clot formation in the sample of blood from the patient, wherein the coagulation characteristic value of the patient that is lower than the coagulation characteristic value that is independent of time of a control (e.g., a healthy volunteer) identifies the patient as likely to require a transfusion of at least six units of blood in six hours.

The invention stems, in part, from the development of the model $$dA/dT = f(A)$$

which is based on taking the derivative of the TEG amplitude (A) parameter over the derivative of Time such that the function f(A) is arrived at. The modeling of this f(A) function allows the prediction of the maximal value of A (MA) based upon the trajectory during the accelerative phase of clot formation.

In some embodiments, the examples below describe the development of this model for f(A).

Thus, in some embodiments, the term "coagulation characteristic value" is meant any value obtained from viscoelastic analysis (e.g., maximum amplitude, LY30, A15).

One non-limiting coagulation characteristic value is Acrit, namely the point at which the rate of change of amplitude is at the maximum. In other words, Acrit is the amplitude at dAmax. Note that Acrit is not the same as MA (or Amax) because just as a moving vehicle does not immediately come to a halt once it stops accelerating, so too the amplitude does not immediately start declining once the rate of change of amplitude stops accelerating.

In some embodiments, the Acrit is obtained at least 10 minutes before the MA is obtained. In some embodiments, the Acrit is obtained at least 15 minutes before the MA is obtained.

As described below, in the examples, the blood of healthy volunteers have fairly high Acrit and modest dAmax. Patients who have significant hemorrhage (i.e., need 6 to 10 units of blood transfused in 6 hours) or massive hemorrhage have lower Acrit than the healthy volunteers. Patients who are injured (e.g., trauma patients) but who do not need more than 6 units of blood transfusion in 6 hours have moderate Acrit but high dAmax.

It should be noted that blood sample of the patient that is being analyzed should be kept on the viscoelastography analyzer, even after the Acrit parameter is taken.

Thus, in some embodiments, the invention uses information based on mathematical analysis of data emitting from a viscoelastic assay device (e.g., a thromboelastograph or a thromboelastometer) to predict whether a patient will require a blood transfusion.

In Example I below, an explanation of the mathematical derivation of Acrit and dAmax is described. Examples II-V describe working embodiments on healthy human volunteers and human patients (e.g., trauma patients).

Example I

In this Example I, a thromboelastoograph (TEG) device commercially obtained from Haemonetics, Corp. (Braintree, Mass.) is used.

Thromboelastography (TEG) is a diagnostic procedure that uses a thin wire probe to measure the strength of blood clots. This measurement is obtained by rotating a sample of blood around the thin wire probe. As the TEG machine rotates the blood, blood clots form and the wire probe adheres to the clot. When the wire probe adheres to the clot, it begins to move with the clot. The movement of the wire probe is recorded as an amplitude in millimeters. Therefore, a patient's clotting ability is directly related to the measured maximum amplitude. Understanding a patient's clotting ability is especially desirable in emergency trauma settings. Disclosed herein is the surprising discovery that the maximum amplitude can be accurately modeled in less time than it takes to measure the maximum amplitude. This can be done by measuring data to a point known as the critical amplitude and deriving the maximum amplitude from this data. An example of data obtained using TEG on a real patient sample is shown in FIG. 7A.

FIG. 7A shows a TEG curve for a healthy human volunteer, namely patient 20074B. As can be seen from FIG. 7A, the amplitude at time t=0 min until t=13.16 min is 0 mm. This is because the blood has not sufficiently clotted to adhere to the wire probe until the split at t=13.16 minutes. Until clotting forms, the wire probe remains motionless, and thus the amplitude is 0. In the art, this period of 0 amplitude may be known as the reaction time or "R value." As the blood sample begins to clot, the wire probe adheres to the moving blood sample and starts moving. As the wire probe moves, the amplitude becomes non-zero.

The amplitude of the wire probe's motion is directly proportional to the strength of the clot. The Amax value is an important factor of a TEG analysis because it indicates the strength of the blood clot i.e., the overall stability of the clot. A computer may record and store the amplitude data as it is collected. The frequency with which amplitude data measurements are taken or sampled is known as the "sampling rate." The sampling rate is easily modified by one having skill in the art, and frequently is a changeable parameter that is part of the data collection software. However, during a single set of data collection, a constant sampling rate is preferable. In other words, the time elapsing between measurements (i) is preferably consistent. For example, the sample rate may be per minute, every second (hertz) or every millisecond (kHz), based on the number of data points and specificity desired. The sample rate may be limited by the maximum sample rate of the device. Alternatively, the sample rate may be dictated by the amount of data that we want to collect. Realistically, time measurements on the plot are shown to fractions of a minute. For example, a split point where the clot starts to form can be measured to t=13.166667 min. The time scale accuracy shows that the sample rate may be fractions of a second.

As data points are collected, it is possible to obtain the rate of change of amplitude (dA/dT). The collection of amplitude data points may be conceptualized as follows:

Amplitude data=$[A_0, A_1, A_2, A_3, A_{N-1}, A_N]$ where $A_1$ is the first amplitude data point collected, $A_2$ is the second amplitude data point collected and so on until N data points have been collected. In this case $A_0$ is the baseline amplitude immediately prior to data collection, e.g. 0.

Each amplitude data point is taken at a corresponding time interval.

Time data=$[T_0, T_1, T_2, T_3, T_{N-1}, T_N]$

Because we can assume that the sampling rate is consistent throughout the entire period of data collection, it should be understood that the time between each measured sample is consistent. Specifically, $\tau = T_1 - T_0 = T_2 - T_1 = T_3 - T_2 = T_N - T_{N-1}$ In other words, if one records 5 samples per second over the course of 30 seconds, 150 data points are obtained with ⅕th of a second between each data point. It should be understood that the time units are dependent upon the sample rate chosen (amplitude values may be collected every millisecond, every second, every minute, etc.).

The rate of change of amplitude per time (dA/dT) for any N-th data point may be conceptualized as follows:

$$\frac{dA_N}{dT} = \left[\frac{A_N - A_{N-1}}{T_N - T_{N-1}}\right]$$

When sampling rate is consistent, the denominator is the same in every equation because the time intervals between all measurements are the same as a result of a consistent sampling rate. The rate of change of amplitude per time (dA/dt) for any N-th data point may be simplified as follows $$\frac{dA_N}{dT} = \left[\frac{A_N - A_{N-1}}{\tau}\right]$$

where $\tau$ is a constant equal to the inverse of the sampling rate, i.e. the time between sampling.

Thus, the parameter $dA_N/dT$ is independent of time.

As shown in FIG. 7A, amplitude rapidly increases after the "split." The rate of change of the amplitude continues to increase until a point labeled Acrit. At Acrit, amplitude increases at the fastest rate. After Acrit, amplitude continues to ascend, but at a slower rate than at Acrit. As the rate of change is calculated over the course of data collection by the computer, it is possible to identify at what time the maximum rate of change (Acrit) occurs. For example, rate of change (dA/dT) values will continue to increase until a maximum rate of change is reached (Acrit), and then rate of change (dA/dT) will decrease. However, just because the rate of change (dA/dT) decreases, it should be noted that amplitude may still be increasing, albeit at a slower rate. A routinely skilled practitioner can review the data emitting from the TEG analysis of a blood sample and detect Acrit, the point at which the rate of change of A stops accelerating and starts slowing down. Of course, a computer can detect that the maximum rate of change (dA/dT) has occurred and identify point Acrit as it occurs.

The amplitude eventually reaches a maximum value, shown as Amax on FIG. 7A. This Amax value provides valuable diagnostic data about the strength of the clot and is also referred to as maximum amplitude (MA) or maximum clot firmness (MCF). In healthy patients, fibrinolysis occurs after Amax, as the wire probe begins to slip, resulting in an amplitude decrease as shown.

In FIG. 7A, Amax occurs approximately 42 minutes after starting the thromboelastography analysis (i.e., putting the blood sample into the TEG machine). The Amax value is approximately 59.02 mm. Because Amax dictates blood clot strength as well as other physiological parameters, in certain emergency patient care situations the sooner Amax can be determined the better. Thus in emergency trauma settings, it is desirable to determine the value for Amax well before the 42 minutes required to reach Amax. As discussed below in Example II, the health and well-being of a trauma patient is assessed at six hours. Therefore, 42 minutes is a very long time to have to wait to determine patient outcome.

Thus, embodiments of the present invention use an empirically derived equation to model Amax from values of Acrit. As a result, Amax (i.e., MA) can be estimated within an accuracy level appropriate to determine relevant physiological factors at the time of Acrit, approximately half the time required to measure Amax.

In some embodiments of the invention, a computer may record amplitude and dA/dT data as discussed above in real time. The data collection may, for example, look something like Table 1 below.

TABLE 1

| Amplitude (mm) | dA/dT (mm/time unit) |
|---|---|
| 10 | 0.60135 |
| 11 | 0.622166 |
| 12 | 0.637843 |
| 13 | 0.648832 |
| 14 | 0.655564 |
| 15 | 0.658451 ($A_{crit}$) |
| 16 | 0.657884 |

As can be seen, when the Amplitude is 15 mm, the rate of change (dA/dT) has reached its maximum (Acrit) at 0.658451 mm/time unit. When the Amplitude is 16 mm, dA/dT begins to descend (note that Amplitude does not descend, only its rate of change (dA/dT) has slowed). In FIG. 7A, Acrit occurs when Amplitude reaches 15 mm at approximately 17 minutes. That is all the time and data that needs to be collected to obtain a calculated Amax using the empirically derived equation described below. As should be understood, obtaining an Amax value from an Acrit value provides a substantial benefit in terms of the time necessary to obtain a value for Amax.

In accordance with the present invention, the inventors have discovered that patient data collected from 161 healthy volunteers could be modeled with empirically derived equation: $dA/dT = aA^2/(e^{bA}-1)$. This equation represents the derivative, or rate of change, of the Amplitude in respect to time. A is the value of the Amplitude, e is a mathematical constant that is approximately 2.71828, a is a patient-specific coefficient derived from fitting that patient's data to the empirically derived equation using a least squares method (a well-established data fitting method), and b is also a patient-specific coefficient derived from fitting that patient's data to the empirically derived equation using a least squares method. To accurately model dA/dT, in some embodiments, the data is collected all the way to point Acrit. After Acrit, the dA/dT equation can be solved for the missing coefficients a and b by a computer in seconds.

Figure 7B:
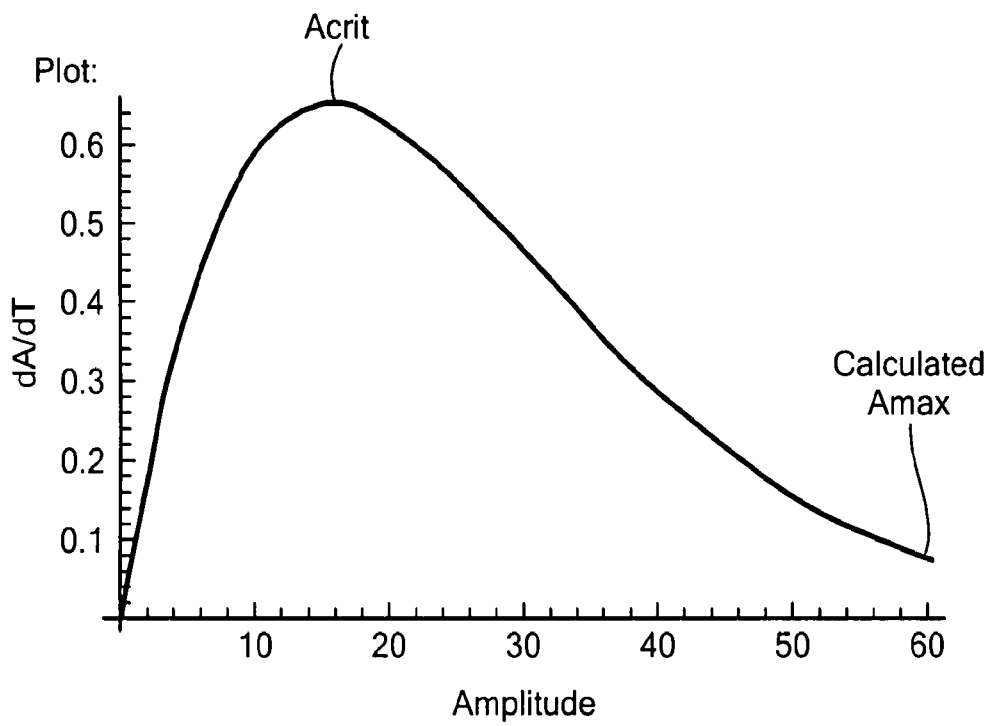
FIG. 7B is a line graph plotting dA/dT against amplitude for $dA/dT=aA^2/(e^{bA}-1)$ with coefficient a=0.011 and coefficient b=0.104 when A goes from 0 to 60.

FIG. 7B is a graph of $dA/dT = aA^2/(e^{bA}-1)$ with coefficient a=0.011 and coefficient b=0.104 when A goes from 0 to 60:

Theoretically, $A_{max}$ should be the point that dA/dT reaches 0. The rate of change (dA/dT) should then become negative to indicate that amplitude is dropping after Amax. Because of the empirical equation chosen, $dA/dT = aA^2/(e^{bA}-1)$, dA/dT will never achieve a negative value unless one of the coefficients is negative. However, in order to fit the model shown, coefficients a and b should both be positive values. A potential issue arises with the use of positive coefficients. Since Amax is the maximum amplitude, all amplitude measurements thereafter should be less than Amax. In other words, the derivative after Amax should be negative. However, as a result of the simplistic equation used to model Amax behavior, certain embodiments of the model may not achieve a negative value for dA/dT. This particular graph of dA/dT v. Amplitude shown in FIG. 7B will only approach dA/dT=0 as Amplitude approaches infinity. However, as we know, Amplitude never actually reaches infinity. Therefore, there may be some specific cutoff threshold value. This value may be set by a computer, for example. For example, setting the requirement that Amax occurs when the change of Amplitude over time eventually slows down to some value, e.g. when dA/dT=0.1.

The coefficients a and b are responsible for determining where the graph of dA/dT will peak, and how quickly it will return to 0 after it peaks. In general terms, coefficient a is responsible for raising the peak of the graph, while coefficient b is responsible for determining how quickly the peak will descend towards 0. Both coefficients are relevant because they influence when dA/dT will reach the cutoff threshold for determining the calculated $A_{max}$ value. A larger a value will result in a correspondingly larger peak value. A larger b value will result in a graph that descends more rapidly. For example, when coefficient a doubles to 0.022, there is a correlated elevation in the peak value, and the calculated $A_{max}$ value, as shown in FIG. 7C.

Figure 7C:
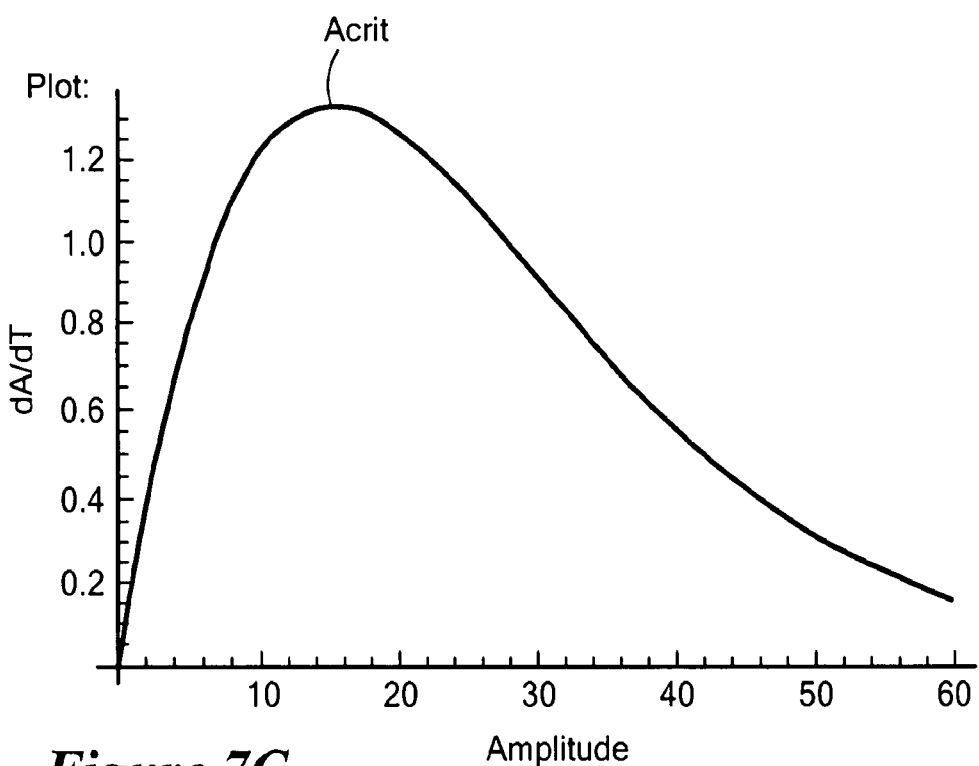
FIG. 7C is a line graph plotting dA/dT against amplitude for $dA/dT=aA^2/(e^{bA}-1)$ with coefficient a=0.022 and coefficient b=0.104 when A goes from 0 to 60.

If a calculated Amax threshold occurs when dA/dT=0.1, the graph shown in FIG. 7C does not extend far enough along the amplitude axis to show what calculated Amax would be i.e. Amax would be greater than 60. The patient having coefficient a value of 0.022 has a quantitatively greater clotting strength than the patient having coefficient a value of 0.011.

Figure 7D:
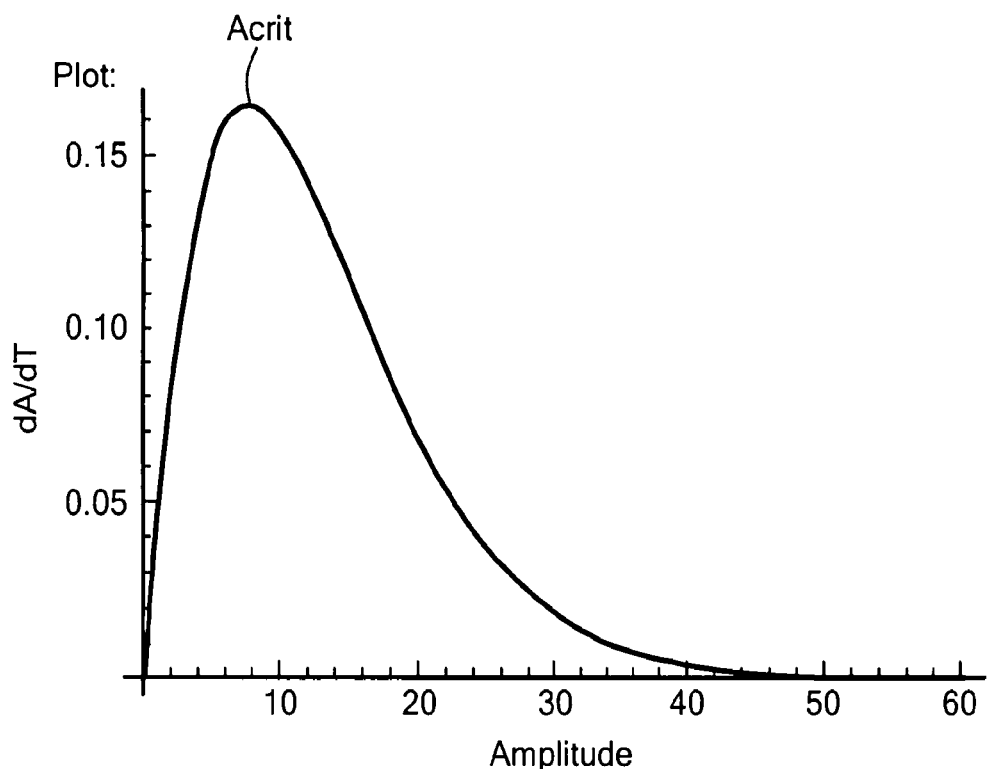
FIG. 7D is a line graph plotting dA/dT against amplitude for $dA/dT=aA^2/(e^{bA}-1)$ with coefficient a=0.011 and coefficient b=0.208 when A goes from 0 to 60.

When coefficient b doubles to 0.208, the graph approaches 0 more quickly as shown in FIG. 7D.

Figure 7E:
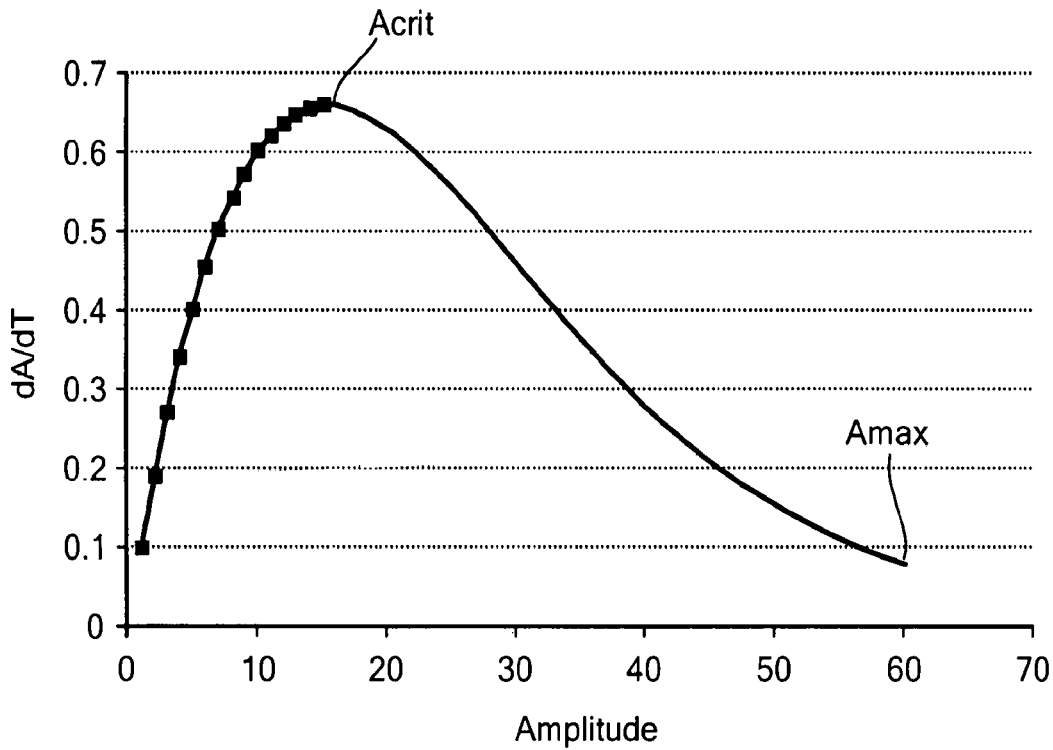
FIG. 7E is a customized model line graph showing the a and b coefficients of patient 20074B (patient data shown as red squares) to create a custom model fitting the patient dA/dT data points against amplitude.

In this case, if calculated Amax were to occur at a threshold when dA/dT=0.1, Amax would occur well before Amplitude=60. In other words, the patient with coefficient b value of 0.208 has significantly weaker clotting than the patient with coefficient b value of 0.104. Noticeably, this increase in coefficient b has dropped the value of Acrit as well. As can be understood, the coefficients do not operate on isolated segments of the graph, but rather work together to produce the entire waveform, including the values for Amax and Acrit. However, as a general concept, a larger a coefficient makes the plot peak larger, and a larger b coefficient brings the plot peak down and causes a more rapid descent towards dA/dT=0. Each a and b coefficient may vary from patient to patient. The a and b coefficients of each patient allow us to create a custom model for each patient based on the Acrit data acquired. For example, as shown in FIG. 7E, data points may be obtained as shown by the squares up until point Acrit.

A program, such as MatLab (commercially available from The MathWorks Inc., Natick, Mass.), may be used to fit the dA/dT data points to the empirically derived equation for dA/dT using the least squares method. Again, the dA/dT data points may be obtained by using the Amplitude data acquired from the TEG procedure. A computer may automatically calculate the dA/dT values.

Amplitude data=$[A_0, A_1, A_2, A_3, A_4, A_{CRIT-1}, A_{CRIT}, A_{CRIT+1}]$

The rate of change of $A_1$ for example is $(A_1-A_0)$ divided by $\tau$, the time between data acquisition measurements.

$$\frac{dA}{dT} = \left[\frac{A_1 - 0}{\tau}, \frac{A_2 - A_1}{\tau}, \frac{A_3 - A_2}{\tau}, \ldots \frac{A_{CRIT} - A_{CRIT-1}}{\tau}, \frac{A_{CRIT+1} - A_{CRIT}}{\tau}\right]$$

The values for dA/dT, that may be obtained using the above equation, are plotted against the Amplitude values up to Acrit. This produces the first part of the waveform up to the peak of the plot. The empirical equation:

$$\frac{dA}{dT} = \frac{a \cdot A^2}{e^{bA} - 1}$$

is then fit to the data points up to Acrit using the least squares method. By fitting the data to the empirical equation, coefficients a and b are determined. This may be done by a computer. Fitting the data to the equation gives coefficients a and b values that produce the best fit to the dA/dT equation using the least squares method. Once the a and b coefficients are obtained from the collected data points up to Acrit, the equation may be extended to Amax. A graph may be used to find the calculated Amax by simply plugging in the best fit a and b coefficients into the dA/dT equation and seeing when the Amax threshold level is reached. As discussed above, the derivative, dA/dT value will approach 0 as Amplitude goes to infinity. This is a property of the model equation chosen. As a result, a trigger threshold dA/dT value may be used to determine when Amax occurs. This trigger threshold can be determined based on empirical data, or when the derivative has reached an adequately low level, for example when dA/dT drops to less than 0.1 mm/time unit.

Example II

The dAmax and Acrit values were obtained from four classes of patients, namely healthy volunteers, trauma patients with no significant bleeding (i.e., hemorrhage), trauma patients with significant hemorrhage needing 6-10 units of blood in 6 hours, and trauma patients with massive hemorrhage needing 10 units of blood in 6 hours or dying of exsanguination in 6 hours.

Blood was collected and analyzed according to standard methods. By way of example, from healthy volunteers, citrated whole blood samples were obtained from healthy volunteers accordingly to standard methods. Similar techniques are performed on blood samples from trauma patients.

Briefly, venipuncture is performed with a 21-gauge needle in an antecubital vein, and blood is collected into evacuated containers containing 3.2% citrate (e.g., a 3.5 mL plastic Vacutainers® containing 3.2% citrate). By a "healthy individual" or "healthy volunteer" is meant a healthy individual who is of reproductive age. For example, if the patient is a human, a healthy volunteer is man or woman between the ages of about 14 years old to about 44 years old, or between about 18 years old to about 40 years old. For each sample of blood, 340 uL of the citrated whole blood (i.e., from the Vacutainers that contained 3.2% citrate) are added to a cup containing 20 μL 0.2 mol/L of $CaCl_2$ and the assay performed on a TEG 5000 Thrombelastograph system (commercially available from Haemonetics, Inc., Braintree, Mass.). Note that if a multi-channel cassette is used, the channel for the particular sample is pre-loaded with 20 μL 0.2 mol/L of $CaCl_2$, to which 340 uL of the citrated whole blood is added.

Table 2 provides the raw data (CRD) from healthy volunteers. Note that in the tables, "CFF" stands for citrate functional fibrinogen TEG, where the extrinsic pathway is activated by the addition of tissue factor and calcium, while the platelet aggregation is inhibited (due to the presence of a monoclonal glycoprotein GPIIb/IIIa receptor antagonist in the Functional Fibrinogen reagent, commercially available from Haemonetics Inc., Braintree, Mass.). Therefore, the CFF number represents the amount of fibrinogen contribution to the strength of the clot. "CFT" is the citrated rapid TEG, which adds kaolin to activate the intrinsic pathway. Thus, the CFT number represents the clot strength as contributed by both platelets and fibrinogen. "CN" is simply native blood or native blood that has been citrated but has no kaolin or tissue factor added. Table 3 provides the healthy volunteer data sorted by CN MA. Table 4 provides the raw data (CRD) from trauma patients sorted by significance of hemorrhage. Table 5 provides the trauma patient data sorted by significance of hemorrhage, where the errors are eliminated. The data from these patients were taken from the TEG apparatus (commercially available from Haemonetics, Corp., Braintree, Mass.) using the computer software provided with the apparatus and additional software for speedy calculations. Note that the data was taken from native TEG (i.e., citrated or non-citrated whole blood without the addition of clotting factors or enhancers of clot formation such as kaolin). These data were then used to calculate Acrit and dAmax values using the equations described above.

Figure 8:
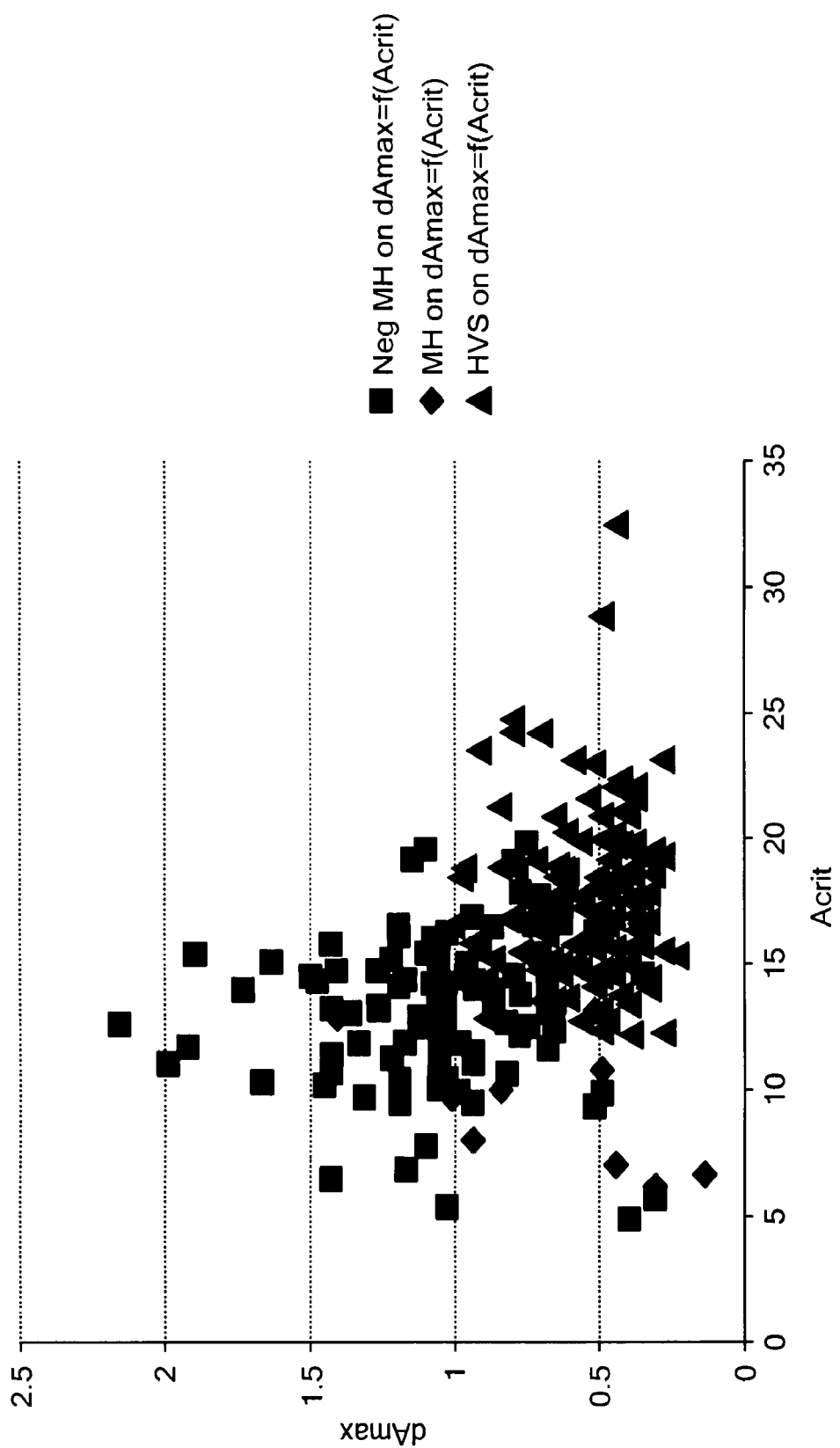
FIG. 8 is a dot plot, showing the dAmax plotted as a function of Acrit. The populations shown are healthy volunteers (light green triangles), trauma patients with negative significant hemorrhage (dark green squares), and trauma patients with massive hemorrhage (needing 10 units of blood in 6 hours, or dying of exsanguination in 6 hours) (orange diamonds).
Figure 9:
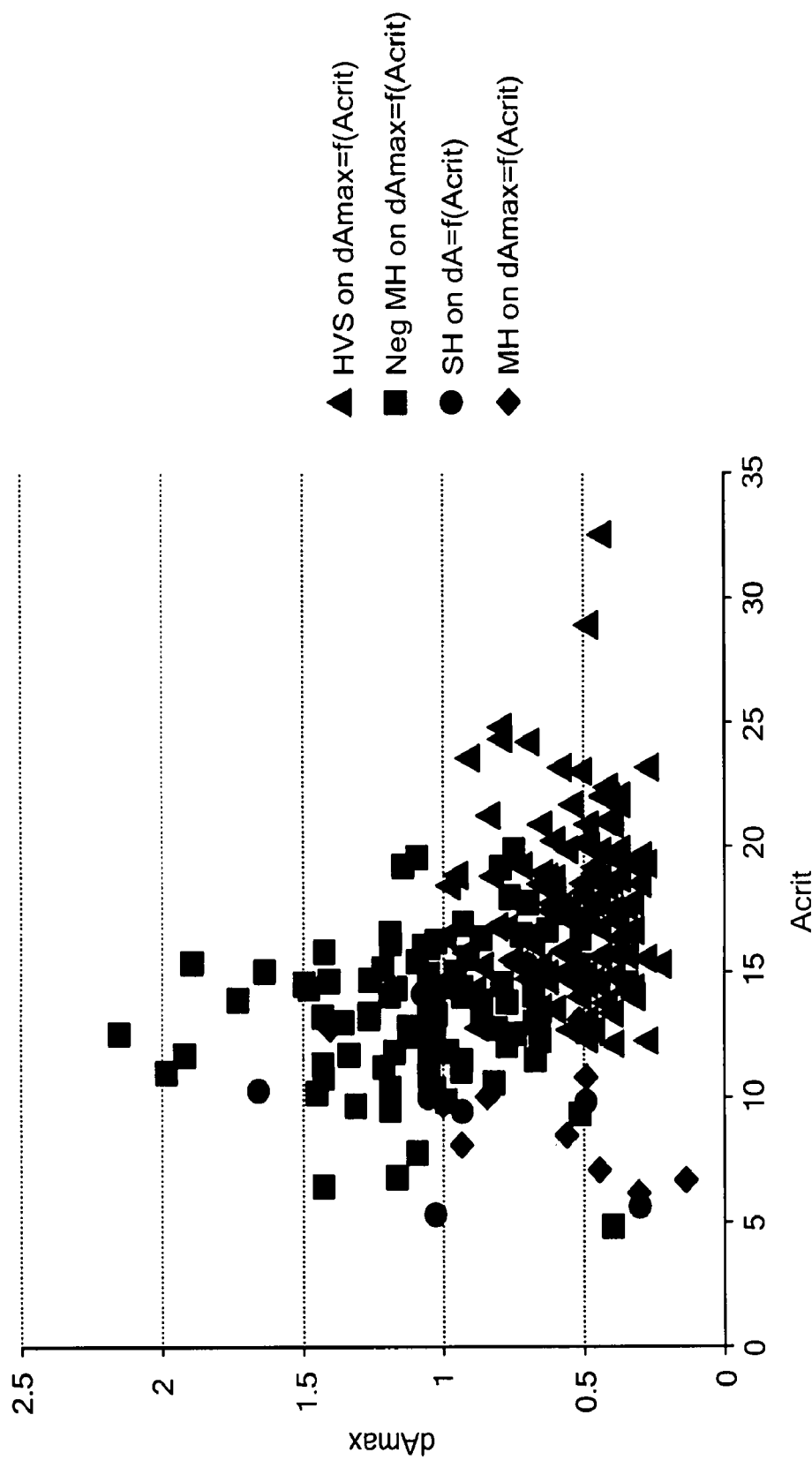
FIG. 9 is a dot plot, showing the dAmax plotted as a function of Acrit. The populations shown are healthy volunteers (light green triangles), trauma patients with negative significant hemorrhage (dark green squares), trauma patients with significant hemorrhage (needing 6-10 units of blood in 6 hours) (yellow circles), and trauma patients with massive hemorrhage (needing 10 units of blood in 6 hours, or dying of exsanguination in 6 hours) (orange diamonds).

In FIGS. 8 and 9, dAmax values were then plotted as a function of Acrit. The data plotted are healthy volunteers (triangles), patients with no massive hemorrhage (squares), patients with significant hemorrhage (circles), and patients with massive hemorrhage (diamonds). A patient with no massive hemorrhage (or no significant hemorrhage) is a patient who does not need more than 6 units of blood in 6 hours. A patient with significant hemorrhage needs between 6 units and 10 units of blood in 6 hours. And a patient with massive hemorrhage is a patient who either needs more than 10 units of blood in 6 hours or less, or who dies of blood loss in 6 hours.

As shown in FIG. 8, patients with massive hemorrhage (orange diamonds) had slightly lower dAmax and slightly lower Acrit values than patients with no significant hemorrhage (blue squares). The difference between both of these populations is striking when compared to healthy volunteers (green triangles) who had higher Acrit values and lower dAmax values. FIG. 9 shows that patients with significant hemorrhage (yellow circles) overlap the patients with massive hemorrhage, but had very little overlap with patients with no significant hemorrhage.

The data is FIGS. 8 and 9 show that healthy volunteers form a tight cluster of fairly high Acrit, and modest dAmax. Furthermore, patients who are injured but do not have significant hemorrhage (i.e., do not require transfusion of more than 6 units of blood in 6 hours) will increase dAmax dramatically (i.e., by increasing generation of thrombin). By doing so, this increase in dAmax in injured patients will shift Acrit values lower. This may be due to the thermodynamic efficiency of clot formation being lower at higher velocity (a common feature of enzymatic chemistry) or simply that there are consumptive processes at work. However, massive bleeders will fail to up-regulate their dAmax and also have a subnormal (i.e., low) Acrit, either from catalysis failure or exhaustion of resources.

Example III

To even more accurately predict the MA, the discontinuity with the model near MA was addressed by taking the area under the tracing and relating it to MA (i.e., Amax). Since there is no closed form solution to relate the MA in the time domain back to the integrated differential equation in the amplitude domain, the relationship will be modeled. By dimensional analysis the solution to the integral of dA/dT with respect to A from A=0 to A=∞ should have units equivalent to $A^2$. Calling this area product "Q", this provided a solution that must be in the form $Q=c(Amax^2)+d$ where c is a function zero order in Amax and T (note that Amax is used synonymously with the time-dependent variable "MA"). The simplest model for this is thus merely a linear fit to existing healthy volunteer and patient data.

The results described here provide the identification of new parameters that can be obtained very early, and that ae reflective of the maximum amplitude. The maximum amplitude is one of the most important predictors of outcomes for trauma patients, and whether or not such patient will require a blood transfusion. In healthy volunteers, the MA occurs typically between about 15 to about 35 minutes after the start of the viscoelastic assay. A lower MA may reflect a hypocoagulable state, such as platelet dysfunction or thrombocytopenia, and thus identifies a patient that is likely to require a blood transfusion. Since the Acrit is reflective of MA, an Acrit that is lower than an equivalent MA at about 15 to about 35 minutes identifies the patient as likely to require a blood transfusion.

Figure 10:
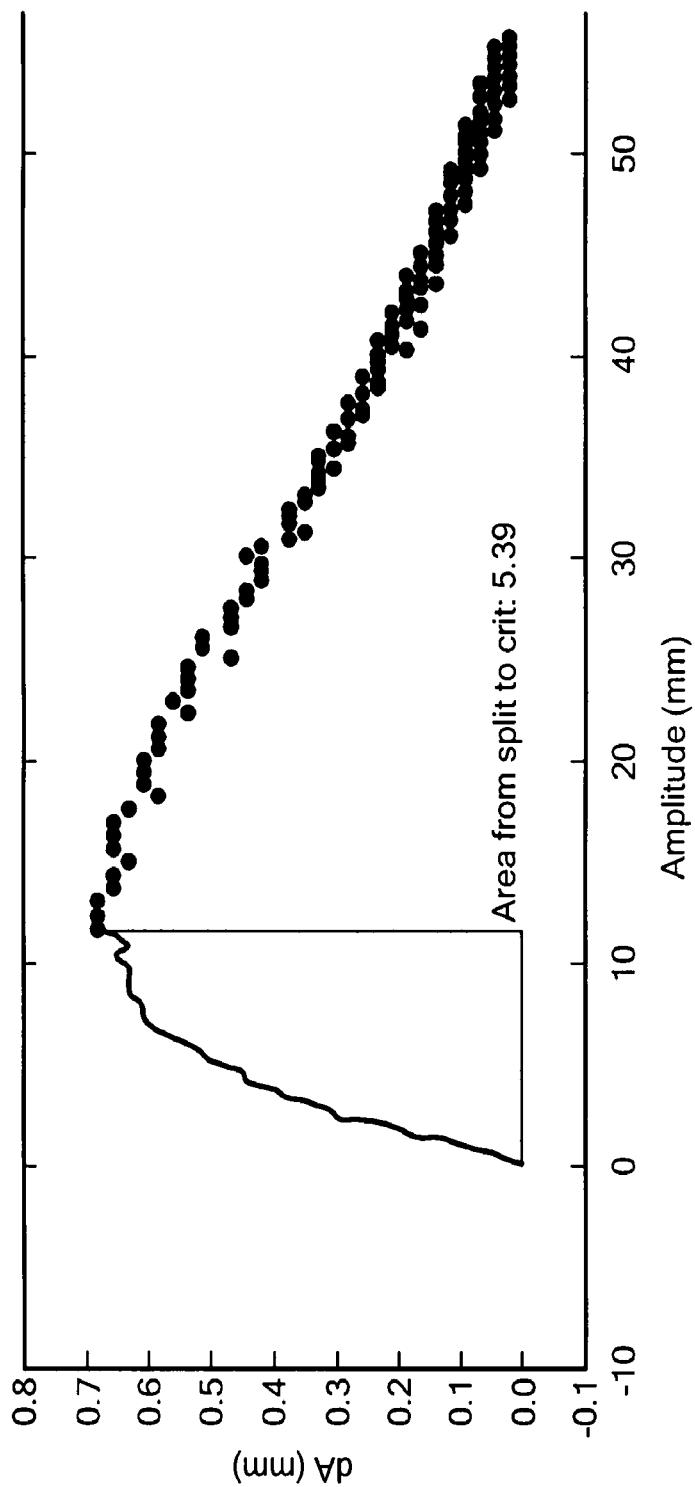
FIG. 10 is a histogram showing the area under the model curve at infinity. The area under the curve (AUC) from the split to the critical amplitude (i.e., the highest dA) is 5.39. Thus, the time-independent TEG AUC (TITAUC) is calculated in the amplitude domain and measures catalysis in the "launch phase" of clotting.
Figure 15:
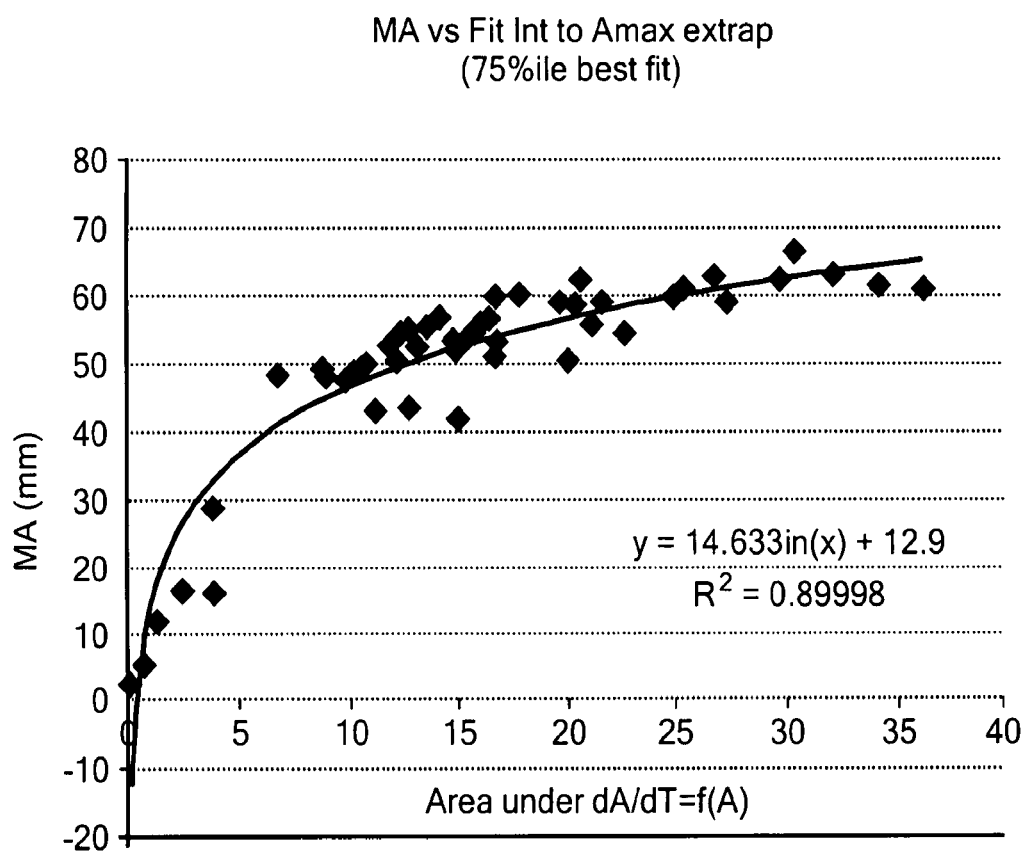
FIG. 15 is a fitting of the data to the model, even when the fit is only to Acrit. This yields the very simple prediction that MA is approximately equal to 15 (ln Q)+12 mm.

As discussed in more detailed in Example IV below, FIG. 15 shows the data points of MA plotted against the area under the curve (see red shaded area in FIG. 10) fit to the model. The area under the curve is clearly shown in FIG. 10 (red shaded area). This red shaded area stops in FIG. 10 at "crit" (i.e., Acrit), which occurs when dA is at its maximum value.

Figure 11:
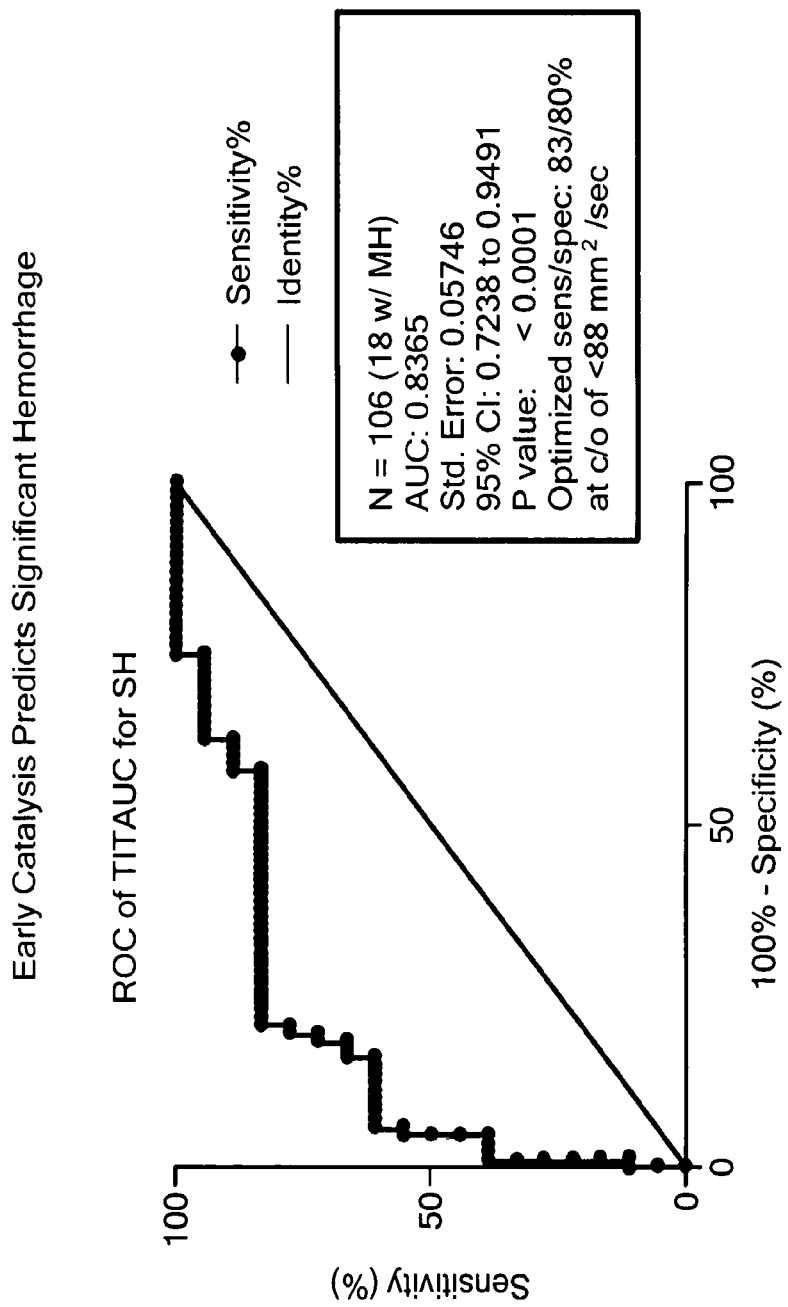
FIG. 11 is a line graph plotting the percent sensitivity versus the percent specificity for the receiver operating characteristic curve (ROC) of the time-independent TEG area under the curve (TITAUC) for patients with significant hemorrhage (i.e., trauma patients who need between 6 to 10 units of blood in 6 hours). As that data shows, quantitation of early catalysis predict those patients with significant hemorrhage.
Figure 12:
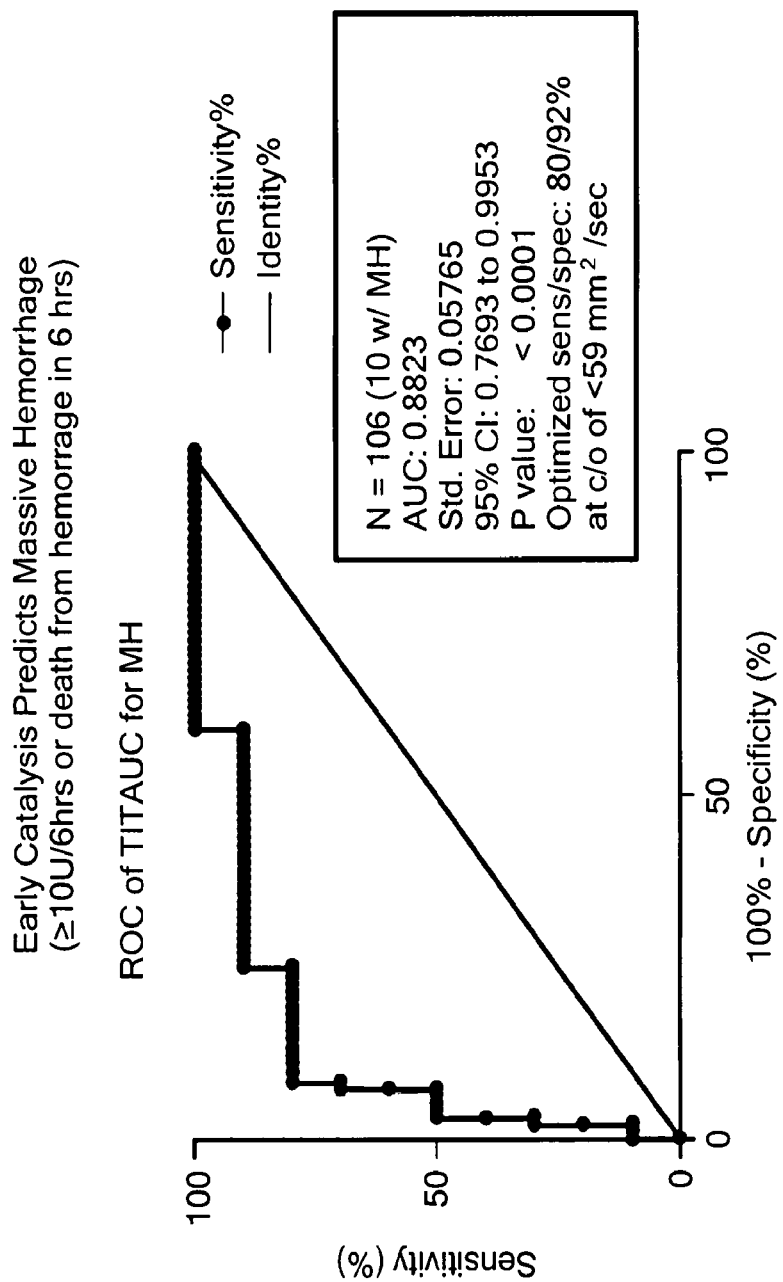
FIG. 12 is a line graph plotting the percent sensitivity versus the percent specificity for the receiver operating characteristic curve (ROC) of the time-independent TEG area under the curve (TITAUC) for patients with massive hemorrhage (i.e., trauma patients who need at least 10 units of blood in 6 hours or less, or bleed to death within 6 hours). As that data shows, quantitation of early catalysis predict those patients with massive hemorrhage.

FIGS. 11 and 12 are two graphs showing the correlation between plotting the % sensitivity versus % specificity for the rate of change of the time-independent TEG area under the curve (TITAUC). The straight diagonal line shows a 50/50 chance of prediction of a patient with significant hemorrhage (FIG. 11) or massive hemorrhage (FIG. 12). Plotting the area under the curve (see FIG. 10), FIG. 11 shows that using the Acrit and dAmax values, a patient with significant hemorrhage could be predicted with an accuracy of 83.65% and FIG. 12 shows that using the Acrit and dAmax values, a patient with massive hemorrhage could be predicted with an accuracy of 88.23%.

Example IV

The MA of a TEG curve is the hypothetical representation of the maximum clot strength which represents a combination of platelet and fibrinogen contributions to the clot's architecture and ultrastructure. However, this MA number is not a simple additive sum, as platelets and fibrinogen are not merely a homogeneous admixture (see FIGS. 5A and 5B). Instead, platelets form nodes in the fibrin network which catalyze the formation of and organize the network as well as actively generating internal stresses by their contraction which enhance the shear and tensile strength of the clot. The complex, non-additive relationship of platelets and fibrinogen to clot strength is exemplified by the fact that an entirely platelet-free clot loses around 80% of its strength, but a fibrinogen free clot loses 100% of its strength.

Thus, simple differential thromboelastography analysis between samples with and without platelet inhibitors is not a fully accurate measure of the individual contributions of platelets and fibrinogen, or more importantly which of these elements is deficient in the setting of a given individual, such as a trauma patient who may or may need a blood transfusion.

To obtain a faster parameter reflective of MA, the TEG tracings of the 161 healthy volunteers were analyzed and more information was extracted from these TEG tracings (also referred to as TEG curves) to obtain novel parameters. These tracing are drawn initially in the time domain (see. e.g., FIG. 4A or 5A), but can be transformed into other coordinate systems that reveal other information encoded in the tracing. For example, the reference frame of the TEG tracings can be arbitrarily shifted to a set of axes which appear to encode the greatest information content.

Another method is to deliberately transform the data into a new set of coordinates may be based on inherent physical properties of the system, for example transforming a complex signal read out in the time domain into the frequency domain to reveal hidden patterns (e.g., a fourier transform).

Similarly, one can transform a signal in the time domain to a signal in the amplitude domain.

Figure 6A:
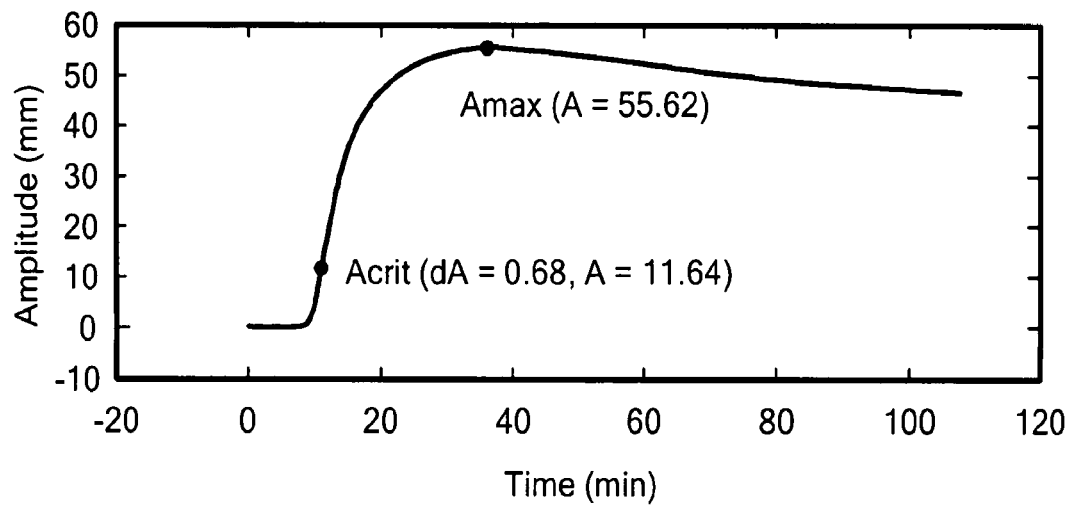
FIGS. 6A-6C is are variations of TEG tracings from a healthy human volunteer.

FIG. 6A, for example, classic TEG tracing of one typical healthy volunteer. In FIG. 4A, time (in min) is on the X axis and amplitude (in mm) is on the Y axis).

Figure 6B:
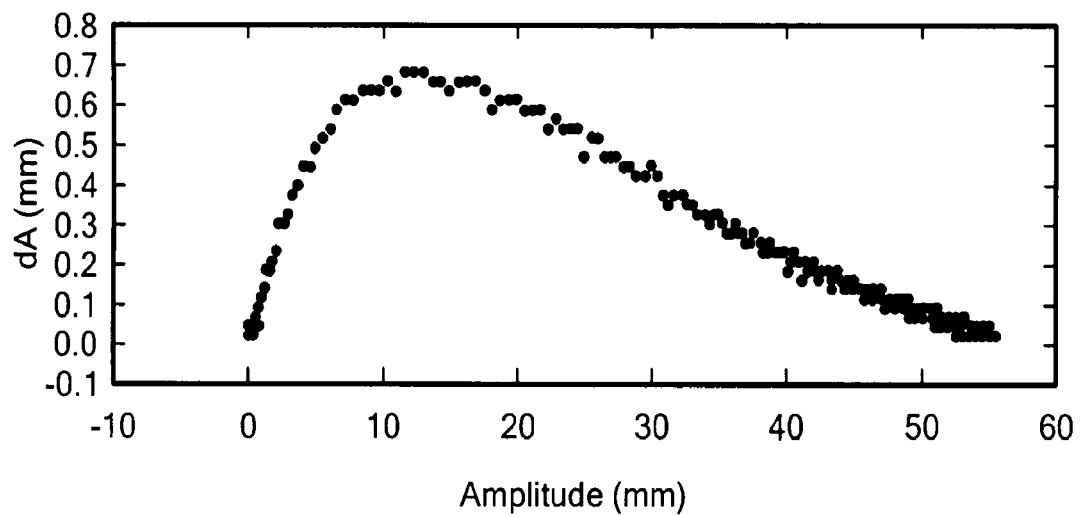

A term of interest, such as the amplitude, can be pulled out of the non-periodic signal (e.g., a TEG tracing) and recast as an independent variable that term (i.e., the amplitude) as the domain, with the rate of change of amplitude as the new dependent variable, dA. This is shown in FIG. 6B. FIG. 6B thus effectively removes the time variable.

Figure 6C:
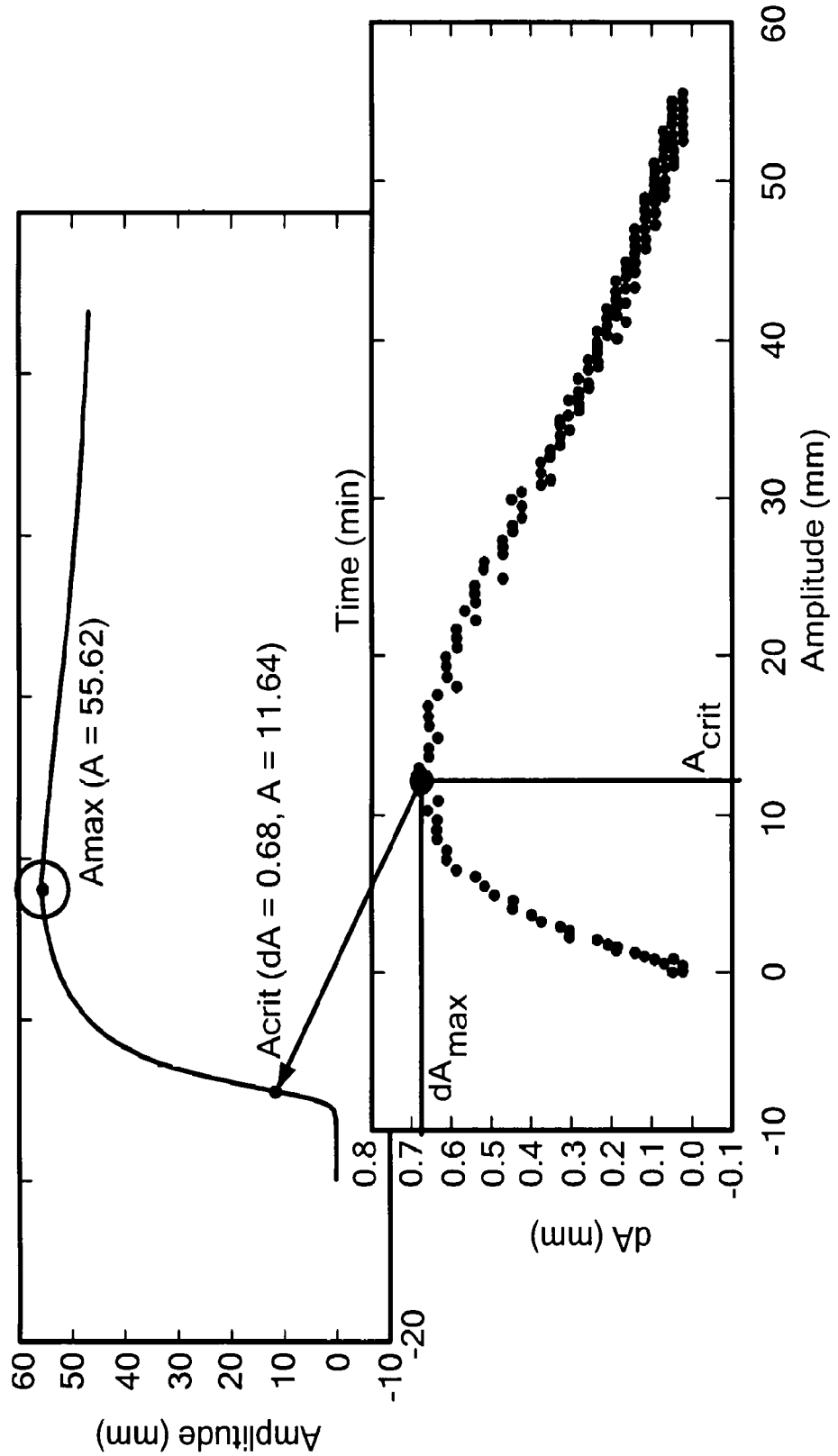

Thus, just as MA is an obvious feature of the time-domain TEG curve, a global maximum exists in the time independent TEG curve. This is called the dAmax for the maximum in the rate of change of A, the corresponding amplitude is called the critical amplitude or Acrit. Acrit is shown on FIG. 6A and FIG. 6C. In FIG. 6C, it is clear that Acrit occurs at dAmax (i.e., at the time that dA is at its maximum value. In the healthy volunteer shown in FIG. 6A, Acrit occurs when the dA is 0.68 and the A is 11.64 mm (see FIGS. 6A and 6C). The Amax is 55.62 mm, and occurs at approximately 38 minutes (see FIG. 6A).

The TEG tracing of another healthy volunteer is shown in FIG. 7A. In FIG. 7A, it is evident that the Acrit parameter is obtainable before 5 minutes after the beginning of clotting (i.e., before the A5 time). In the patient shown in FIG. 7A, the A5 parameter (i.e., 5 minutes after clotting) is obtained 18.17 minutes after the start of the TEG assay. However, the Acrit parameter is obtained at approximately 17 minutes after the start of the assay.

Thus, in some embodiments, the invention provides a parameter for detecting whether or not a patient will need a blood transfusion less than 5 minutes after the blood starts clotting in a viscoelastic assay. In some embodiments, the invention provides a parameter for detecting whether or not a patient will need a blood transfusion less than 10 minutes after the blood starts clotting in a viscoelastic assay. In some embodiments, the invention provides a parameter for detecting whether or not a patient will need a blood transfusion less than 15 minutes after the blood starts clotting in a viscoelastic assay.

In some embodiments, the invention provides a parameter for detecting whether or not a patient will need a blood transfusion less than 18 minutes after the start of the viscoelastic assay (i.e., after the blood sample from the patient is placed into the viscoelastic analyzer for analysis). In some embodiments, the invention provides a parameter for detecting whether or not a patient will need a blood transfusion less than 20 minutes after the start of the viscoelastic assay. In some embodiments, the invention provides a parameter for detecting whether or not a patient will need a blood transfusion less than 25 minutes after the start of the viscoelastic assay. In some embodiments, the invention provides a parameter for detecting whether or not a patient will need a blood transfusion less than 30 minutes after the start of the viscoelastic assay.

Figure 13:
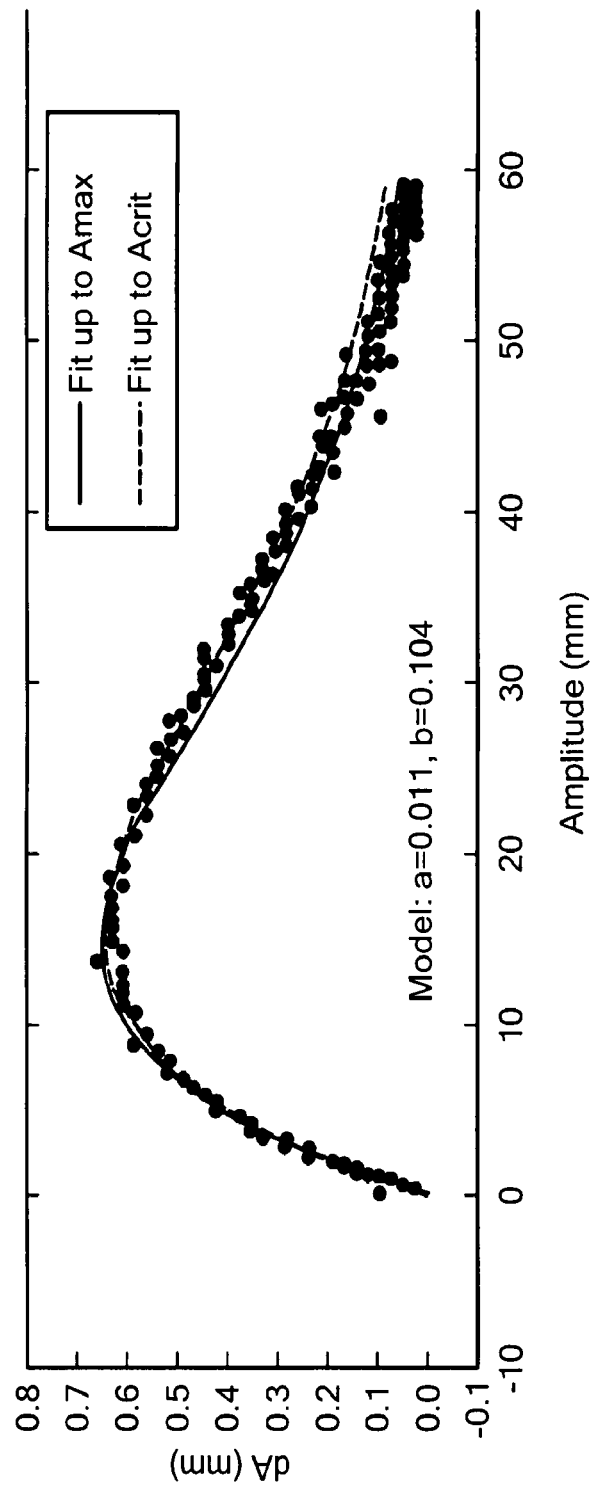
FIG. 13 is the tracing of the derivative of the amplitude of FIG. 7A fitted to the Amax curve (green line) and the Acrit curve (red line). As can be seen, with these two parameters, the fit is extremely close.

FIG. 13 shows that the mapping of Acrit and Amax parameters of the tracing of FIG. 7A in a Planck-like fit is stable. (See red line in FIG. 14A, fit up to the maximum at Acrit).

The behavior in the TEG tracings suggests some degree of coupling with some hidden variables. Pulling these hidden variables out requires integrating this differential equation:

$$dA/dT = f(A)$$

This equation is an implied function and is clearly a non-linear differential equation even in the case of the simplest model. So solving in closed form is likely not possible and there is a good chance that its expansion will not converge.

Note that initially the TEG tracings from the healthy volunteers were modeled with the empirically derived equation $$dA/dT = aA^2/(e^{bA} - 1)$$

Fitting to this model equation was used to test the robustness of the fit. The same fitting was done, varying only a and b, to only the accelerative phase of the curve, prior to the maximum value of dA (dAmax).

As a first step to deriving this model, a curve fitting was attempted as a methodology for prediction of early from late (notably attempts to do this in the time domain have been notoriously unsuccessful). The goal was to develop the simplest possible model for interpolation and extrapolation in order to avoid the pitfalls of overfitting. Furthermore, the model developed is based on other natural phenomena not simply a polynomial. Thus, a lower order modification of Planck's equation on this basis, as it contains only 2 fitting parameters in its simplest form. These are shown in FIG. 13, and the fit on the two parameters (Acrit and Amax) is stable.

Figure 14:
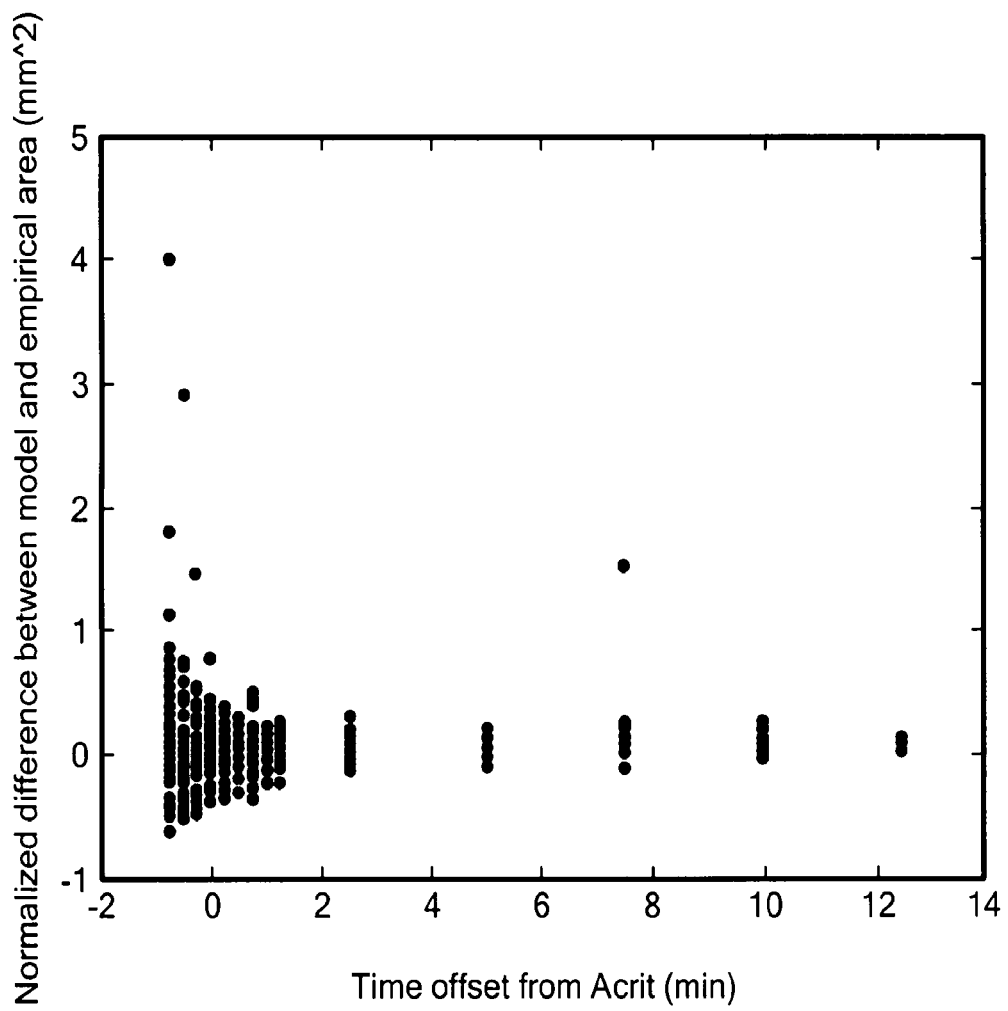
FIG. 14 is a scatter plot showing the convergence of the fit with increasing data, plotting time offset from Acrit (min) on the x-axis and normalize difference between model and empirical area ($mm^2$) on the y-axis.

However, as shown in FIG. 14, the fit converges with increasing data. This convergence is an important characteristic of predictive stability. On the x axis in FIG. 14 is the time off-set from Acrit in minutes. As time increases, there is an increasing progression of inclusion of data points in the TEG tracing. 0 on the x-axis in FIG. 14 is Acrit. On the y-axis in FIG. 14 is the normalized difference in area under the curve between the model and the actual Amplitude domain data. Note that this is simply a convenient representation of the aggregate error of the fit. The root mean square deviation (or root mean square error) (RMSE) for each point can also be used to obtain an equivalent result.

As FIG. 14 shows, the more the TEG curve is allowed to progress before attempting the fit, the better the prediction, but this rapidly converges near Acrit. This increasing fit and the rapid convergence near Acrit provides that the model is sound.

Thus, in many individuals' TEG tracings, the accelerative phase fit was nearly superimposable with the full tracing fit all the way to MA. Interestingly, even when the least squares fit is poor, the two model trajectories appear to converge at MA (see FIG. 13). This is suggestive that there is a valid physical basis to the trajectory equation. However, the behavior of the time-independent TEG tracing (TITT) and the model diverge near MA (see FIG. 13). This is because the actual TITT is not smooth in this limit, and is no longer a explicitly definable function as it doubles back on itself as the curve decays based on physical processes distinct from its formation, whereas the model is asymptotic at the X-axis (i.e. in the model the clot grows forever albeit at rate limit 0 at infinity).

To map this back to the MA, since the model is asymptomatic at the x-axis, no explicit coordinate pair defines MA. Therefore, this is analogous to infinite, infinitely slow growth of the clot. The model $$dA/dT = aA^2/(e^{bA} - 1)$$

is solved, yielding A(t). Theoretically A(t) could then be evaluated at infinity to yield the MA, but of course this is not possible.

Instead the area under the model curve at infinity is evaluated which should have units of mm-squared per second which obviously yields infinite amplitude when evaluated at T=infinity. This can be done by taking the area under the tracing and relating it to MA. Since there is no closed form solution to relate the MA in the time domain back to the integrated differential equation in the amplitude domain, the relationship will be modeled. By dimensional analysis, the solution to the integral of dA/dT with respect to A from A=0 to A=∞ should have units equivalent to $A^2$. Calling this area product "Q", this provided a solution that must be in the form $Q = c(A_{max}^2) + d$ where c is a function zero order in Amax and T (note that Amax is used synonymously with the time-dependent variable "MA"). The simplest model for this is thus merely a linear fit to existing healthy volunteer and patient data.

In fact, the area under the curve converges itself and should have an explicit relation (albeit unknown) to the solution to the differential equation which must include this integral. Thus, evaluated the explicit integral, a and b are unitless constants and yield a result in terms of Amplitude squared.

$$\int_0^\infty \frac{aA^2}{e^{bA}-1} dA$$

Therefore, a function of this area was hypothesized to yield MA. This was then tested against the actual data.

As shown in FIG. 15, this relationship is stable even when the fit is run only to Acrit and yields the very simple prediction:

MA is approximately equal to 15 (ln Q)+12 mm

The test for fit was on a subset of the actual human data where the original curve fit was good (see FIG. 15). Note that the "goodness" of the curve fit was not being tested. Rather, the test was whether the hypothesis that MA bears an explicit mathematical relation to the integral in question was plausible. Our test revealed that the MA clearly bears an explicit mathematical relation to the integral. This appears to conform to a logarithmic fit but it is actually more likely a fractional power.

Thus, these studies show that Acrit occurs very early—even before the A5 min or A10 min marks which some practitioners advocate as a means of early estimation of MA (see FIG. 7A). Note that FIG. 7A (and FIG. 6A) is a native tracing which accounts for the long R-time.

With these new parameters (e.g., Acrit, and dA), numerous objectives can be achieved in the quest to predict late TEG events in a very rapid fashion.

Example V

Massive hemorrhage is a significant cause of death in trauma patients. However, all the information needed to determine if a patient (e.g., a trauma patient) will require a large blood transfusion within six hours (or die) is contained within a blood sample taken from that patient. Currently, some of the best indicators of significant or massive hemorrhage in the patient take over 40 minutes to obtain (i.e., the MA value). The methods described herein, and the new parameters (e.g., dAmax and Acrit) allow accurate prediction of the MA in a much fast time (e.g., less than twenty, or less than fifteen, or less than ten, or less than five minutes after the start of the viscoelastic assay).

In addition, the methods and parameters described herein are useful for determining what part of the coagulation process is not functioning normally in a patient who might experience significant or massive hemorrhage. As discussed above, hemostasis is a complicated, tightly regulated process involving multiple factors (see FIG. 1). The intrinsic pathway to coagulation is initiated by providing a surface on which the clotting factors can aggregate. To do this using a viscoelastic assay, reagents such as kaolin are added to provide that surface. This surface contact can activate Factor XII to form Factor XIIa which then activates Factor XI to form Factor XIa. In other words, the surface of kaolin is acting like Kininogen and kallikrein in FIG. 1. The extrinsic pathway is the tissue factor pathway, and provides a thrombin burst during traumatic injury. As shown in FIG. 1, trauma acts via Factor VIIa and tissue factor to activate Factor X to form Factor Xa.

Platelets also play a role in clot formation. During injury, platelets immediately form a plug at the injury site. The clotting cascade pictured in FIG. 1 occurs simultaneously, and contributes fibrin to strengthen the clot. Thus, platelets and fibrin (and its precursor, fibrinogen) contribute to clot strength; however, their contributions are not additive (see FIGS. 3A and 3B). It would be useful, however, to determine if problems with clotting are due to the fibrin contribution or the platelet contribution, because identifying the source of the problem could lead to better patient treatments. For example, if the lack of clotting was the result of low platelet activation, the patient could be treated with a platelet activator such as Factor VIIa, desmopressin, and thrombopoietin and thrombopoietin mimetics. Conversely, if the lack of clotting was the result of low fibrinogen activation to produce fibrin, the patient could be treated with thrombin and/or fibrinogen to increase fibrin production.

Figure 16:
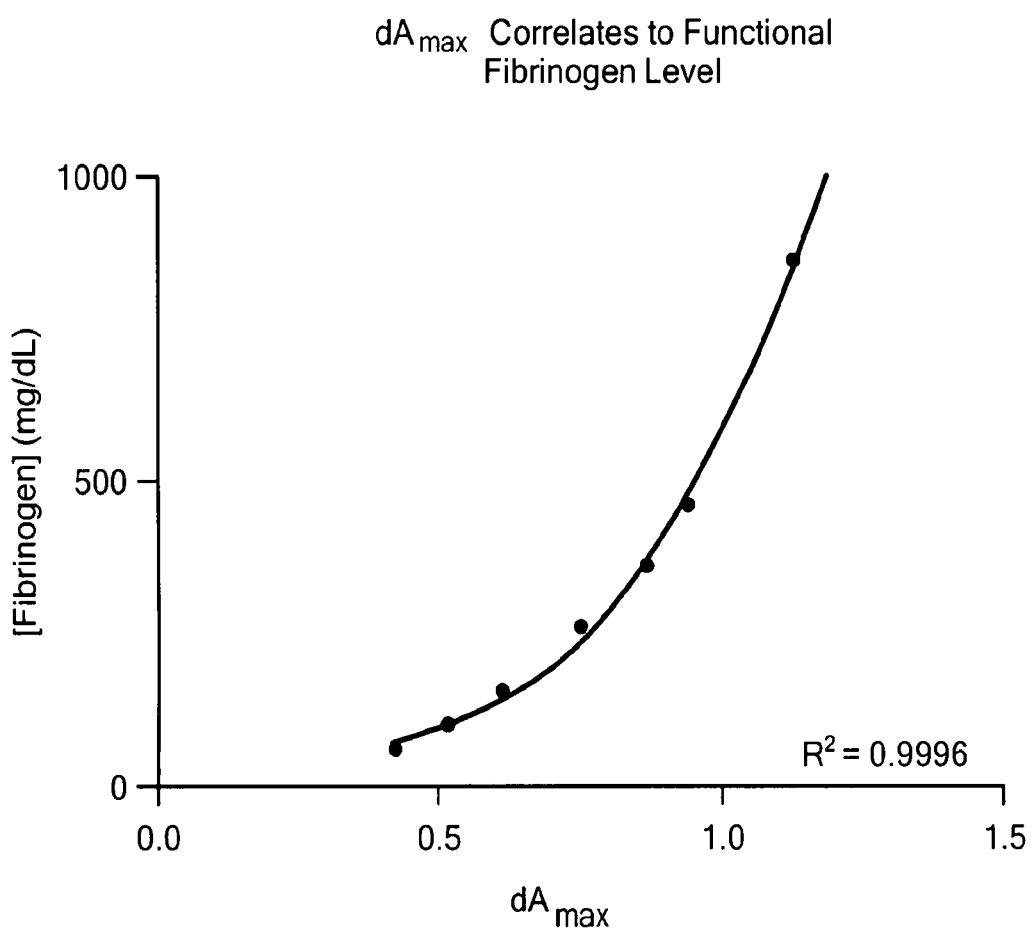
FIG. 16 is a scatter plot demonstrating sigmoid relation of dAmax to the amount of fibrinogen is a blood sample.

Surprisingly, the methodologies described herein are able to detect contributions of fibrinogen to clot strength, and are able to detect contributions of platelets to clot strength. In FIG. 16, increasing amounts of fibrinogen are added to a blood sample ranging from the hypo to hypercoagulable range while platelet count is held constant. These spiked samples were subjected to viscoelastic analysis, and the dAmax values plotted against the amount of added fibrinogen. As shown in FIG. 16, fibrinogen activity demonstrated a very tightly correlated sigmoid relationship to dAmax. In other words, in an artificial system (i.e., using spiked blood), dAmax was found to be correlative to functional fibrinogen level, and therefore is a marker of the contribution of fibrinogen (and fibrin) to a blood clot.

Figure 17:
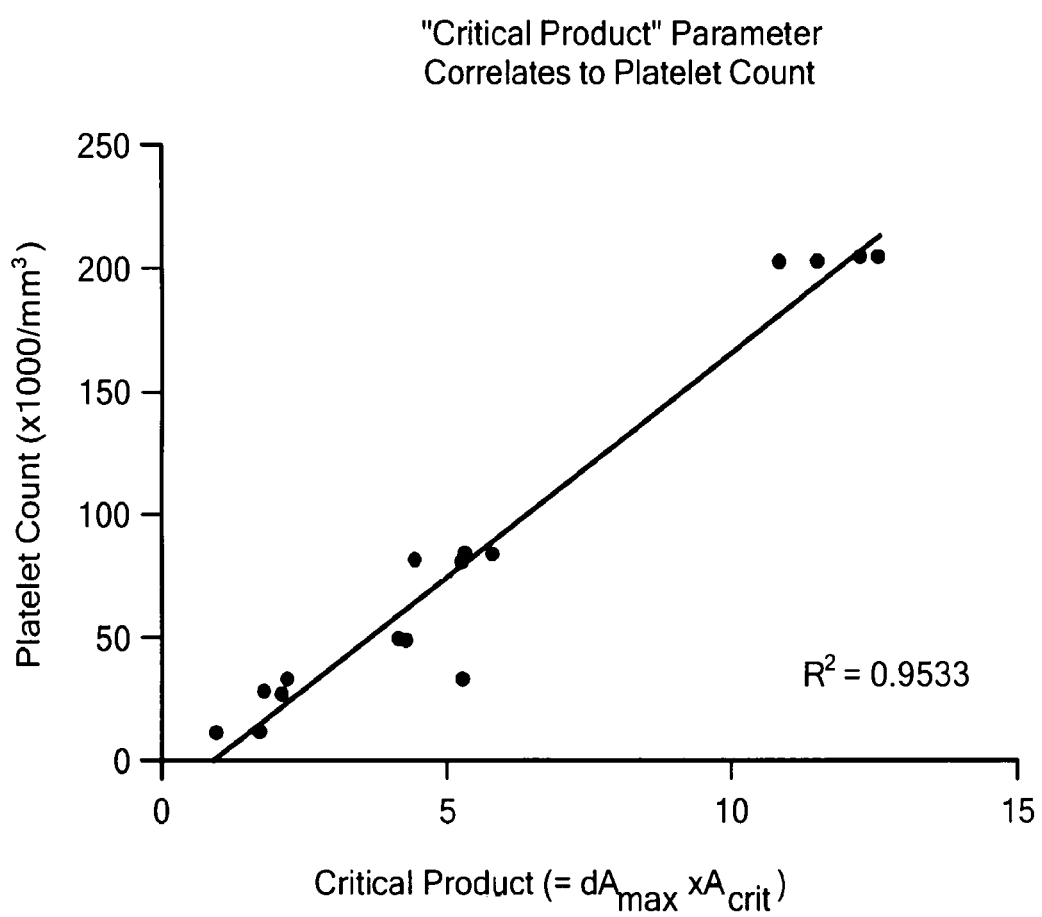
FIG. 17 is a scatter plot showing that a product of dAmax multiplied by Acrit (the "critical product") is correlates linearly with the number of platelets in a blood sample.

Similarly, in order to derive correlates of time-independent TEG parameters to total platelet function, another artificial system was set up in which platelets were depleted from whole blood by differential centrifugation, and then counted. The blood samples containing various amounts of platelets were then subjected to viscoelastic analysis and the dAmax value multiplied by the Acrit value to arrive at a "critical product". This "critical product" value was plotted against the number of platelets in the sample in FIG. 17, and the resulting graph shows a clear linear relationship between the product of dAmax and Acrit (the "critical product") and total platelet count.

Thus, using the methods and parameters identified herein allows the dissection of the blood clotting into the contributions of fibrinogen and platelets.

Figure 18:
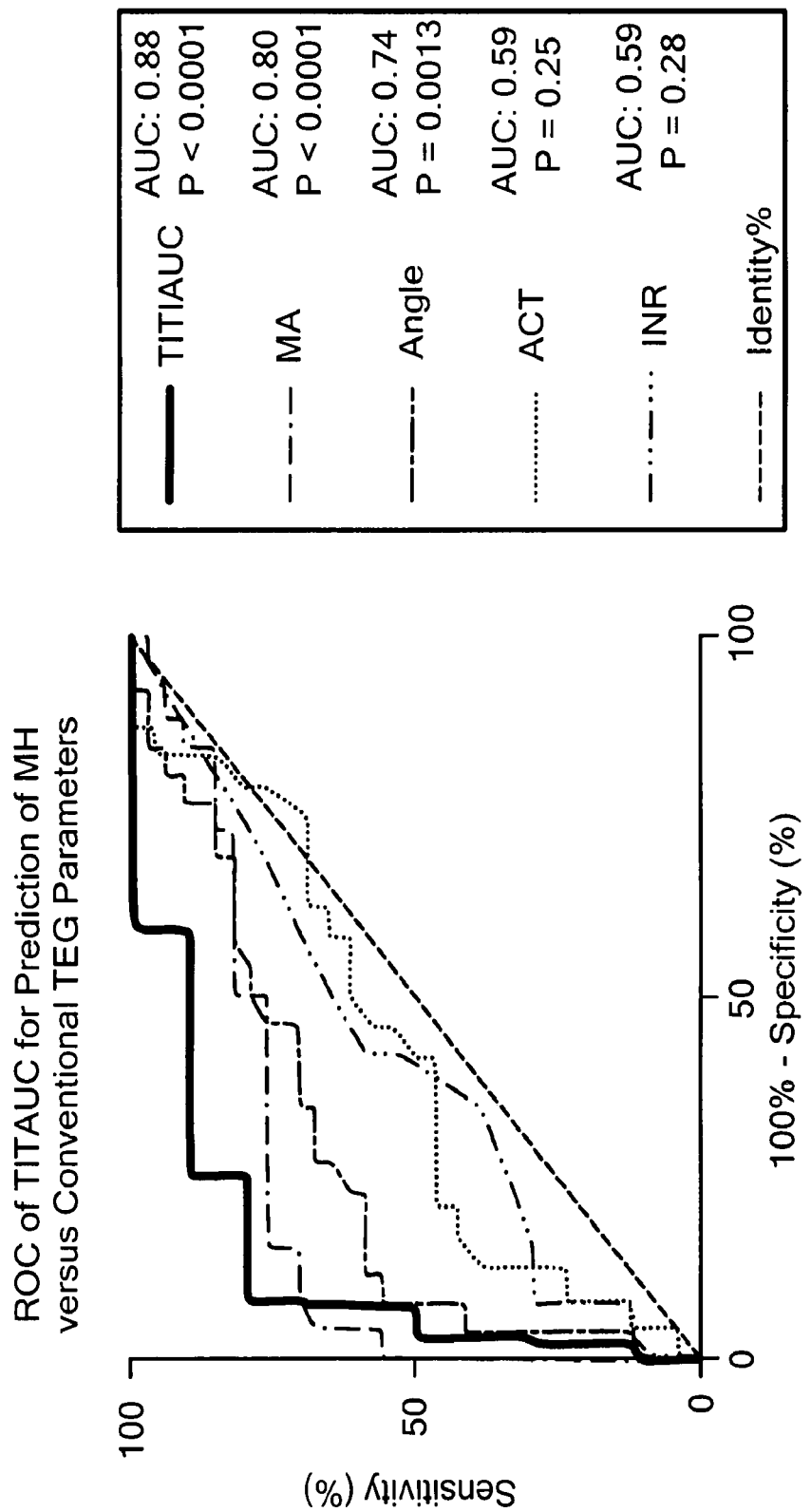
FIG. 18 is a line graph showing receiver operating characteristic curve (ROC) of the time-independent TEG area under the curve (TITAUC) for patients with massive hemorrhage as compared to conventional TEG parameters. As can be see, the area under the curve (AUC) for time-independent TEG (blue line) has a higher identity for predicting massive hemorrhage than the AUC for MA (red line), the AUC for the alpha angle (purple line), the AUC for activated clotting time (ACT) (brown line) and the AUC for the International Normalization Ratio (INR) (green line).

Finally, as shown in FIG. 18, the area under the receiver operating characteristic curve (ROC) of the time-independent TEG (TITAUC) for patients with massive hemorrhage is more accurate at predicting patients who will suffer massive hemorrhage compared to the AUC for maximum amplitude (MA; red line), the AUC for the alpha angle (purple line), the AUC for activated clotting time (ACT; brown line) and the AUC for the International Normalization Ratio (INR) (green line).

The embodiments of the invention described above are intended to be merely exemplary; numerous variations and modifications will be apparent to those skilled in the art. All such variations and modifications are intended to be within the scope of the present invention as defined in any appended claims.

The invention claimed is:

1. A method of treating a subject in need of a blood transfusion comprising:
(a) analyzing a sample of blood from the patient with a viscoelastic analysis to obtain a patient coagulation characteristic value that is independent of time,
wherein the patient coagulation characteristic value
(i) is at least 1.5 times lower than a control coagulation characteristic value that is independent of time, and
(ii) is obtained by fitting a tracing from the viscoelastic analysis of the same sample of blood from the patient to a tracing from the model $dA/dT=aA^2/(e^{bA}-1)$,
wherein:

dA/dT represents change in amplitude over change in time and the first derivative of a tracing of the viscoelastic assay with respect to time, A represents amplitude from a tracing of the viscoelastic assay, a and b are both patient-specific coefficients calculated using least-squares method of fitting the patient data to the model, and e is the mathematical constant approximately equal to 2.71828; and (b) transfusing at least six units of blood to the patient within six hours or less after obtaining the patient coagulation characteristic value, wherein the patient coagulation characteristic value is obtained not more than twenty minutes after the start of the viscoelastic analysis.

2. The method of claim 1, wherein the control coagulation characteristic value is obtained by analyzing a sample of blood from a control with a viscoelastic analysis.

3. The method of claim 2, wherein the control is a healthy volunteer.

4. The method of claim 2, wherein the control is a population of patients and the control coagulation characteristic value is the mean coagulation characteristic value of the population.

5. The method of claim 1, wherein the sample of blood is not supplemented with a clotting factor or an enhancer of clot formation.

6. The method of claim 1, wherein the patient or control coagulation characteristic value is Acrit, wherein Acrit corresponds to an amplitude (A) of a tracing produced by the viscoelastic assay at which a maximum in the rate of change in amplitude occurs.

7. The method of claim 1, wherein the patient or control coagulation characteristic value is dAmax, wherein dAmax corresponds to a maximum in the rate of change in amplitude (A) of a tracing produced by the viscoelastic assay, wherein dAmax is calculated by taking the first derivative of the tracing to obtain change in amplitude over change in time, and wherein dAmax is the maximum of the values calculated from the derivative.

8. The method of claim 1, wherein the patient coagulation characteristic value is obtained not more than fifteen minutes after the start of the viscoelastic analysis of the sample of blood from the patient.

9. The method of claim 1, wherein the patient coagulation characteristic value is obtained not more than five minutes after the start of the viscoelastic analysis of the sample of blood from the patient.

10. The method of claim 1, wherein the patient coagulation characteristic value is obtained not more than fifteen minutes after the start of clot formation in the sample of blood from the patient.

11. The method of claim 1, wherein the patient coagulation characteristic value is obtained not more than five minutes after the start of clot formation in the sample of blood from the patient.

12. The method of claim 1, wherein the viscoelastic assay is performed using thromboelastography.

13. The method of claim 1, wherein the viscoelastic assay is performed using thromboelastometry.

14. The method of claim 1, wherein the method comprises identifying the patient as requiring a transfusion of at least six units of blood within six hours or less after obtaining the patient coagulation characteristic value.

15. The method of claim 1, wherein the patient coagulation characteristic value is obtained by transforming a data set from the viscoelastic analysis reported in the time domain to a data set in the amplitude domain and fitting the data set in the amplitude domain to the model $dA/dT=aA^2/(e^{bA}-1)$.

16. The method of claim 1, wherein the patient coagulation characteristic value is obtained by taking an area under a tracing from the viscoelastic analysis of the same sample of blood from the patient from a start of clot formation to a maximum amplitude.

17. The method of claim 1, further comprising administering to the patient a transfusion of at least ten units of blood within six hours or less after obtaining the patient coagulation characteristic value.

* * * * *